(12) United States Patent
Fallin et al.

(10) Patent No.: US 10,258,401 B2
(45) Date of Patent: Apr. 16, 2019

(54) TRANSOSSEOUS GUIDE

(71) Applicant: KATOR, LLC, Logan, UT (US)

(72) Inventors: T. Wade Fallin, Hyde Park, UT (US); Joel Helgerson, Erie, CO (US)

(73) Assignee: KATOR, LLC, Logan, UT (US)

( * ) Notice: Subject to any disclaimer, the term of this patent is extended or adjusted under 35 U.S.C. 154(b) by 67 days.

(21) Appl. No.: 15/211,764

(22) Filed: Jul. 15, 2016

(65) Prior Publication Data

US 2017/0014172 A1    Jan. 19, 2017

Related U.S. Application Data

(60) Provisional application No. 62/193,888, filed on Jul. 17, 2015.

(51) Int. Cl.

| | | |
|---|---|---|
| *A61F 2/08* | (2006.01) | |
| *A61B 17/88* | (2006.01) | |
| *A61B 17/16* | (2006.01) | |
| *A61B 17/17* | (2006.01) | |
| *A61B 90/00* | (2016.01) | |

(52) U.S. Cl.
CPC ...... *A61B 17/8861* (2013.01); *A61B 17/1604* (2013.01); *A61B 17/1778* (2016.11); *A61B 17/1796* (2013.01); *A61B 90/06* (2016.02); *A61B 17/1684* (2013.01); *A61B 17/1714* (2013.01); *A61B 2090/062* (2016.02)

(58) Field of Classification Search
CPC ........................... A61B 17/8611; A61F 2/0805
See application file for complete search history.

(56) References Cited

U.S. PATENT DOCUMENTS

| | | | |
|---|---|---|---|
| 1,583,271 A | 5/1926 | Ladislaus | |
| 1,856,721 A | 5/1932 | Nagelmann | |
| 4,312,337 A * | 1/1982 | Donohue | A61B 17/1796 606/103 |
| 4,441,497 A | 4/1984 | Paudler | |
| 4,622,960 A | 11/1986 | Tam | |
| 4,672,957 A | 6/1987 | Hourahane | |
| 4,738,255 A | 4/1988 | Goble | |
| 4,741,330 A | 5/1988 | Hayhurst | |
| 4,784,126 A | 11/1988 | Hourahane | |
| 4,809,408 A | 3/1989 | Abrahamson | |
| 4,898,156 A | 2/1990 | Gatturna | |
| 4,959,069 A | 9/1990 | Brennan | |

(Continued)

FOREIGN PATENT DOCUMENTS

| | | |
|---|---|---|
| WO | WO1998006344 A1 | 2/1998 |
| WO | WO2003065904 A1 | 8/2003 |

(Continued)

OTHER PUBLICATIONS

Comprehensive Product Offerings for your Rotator Cuff Repair, Smith & Nephew, Inc., www.smith-nephew.com, 2015, 12 pp.

(Continued)

*Primary Examiner* — Jan Christopher L Merene
(74) *Attorney, Agent, or Firm* — David Meibos; Maywood IP Law

(57) ABSTRACT

Instruments and methods for surgical transosseous attachment to a bone include a guide able to guide the formation of intersecting bone tunnels and a passer able to pass a member through the bone tunnels.

30 Claims, 21 Drawing Sheets

(56) References Cited

U.S. PATENT DOCUMENTS

| | | |
|---|---|---|
| 5,037,422 A | 8/1991 | Hayhurst |
| 5,041,129 A | 8/1991 | Hayhurst |
| 5,100,417 A | 3/1992 | Cerier |
| 5,176,682 A | 1/1993 | Chow |
| 5,224,946 A | 7/1993 | Hayhurst |
| 5,236,445 A | 8/1993 | Hayhurst |
| 5,250,055 A | 10/1993 | Moore |
| 5,254,126 A | 10/1993 | Filipi |
| 4,890,615 A | 11/1993 | Caspari |
| 5,257,996 A * | 11/1993 | McGuire ............. A61B 17/15 606/104 |
| 5,258,016 A | 11/1993 | DiPoto |
| 5,268,001 A | 12/1993 | Nicholson |
| 5,269,809 A | 12/1993 | Hayhurst |
| 5,312,438 A | 5/1994 | Johnson |
| 5,336,240 A | 8/1994 | Metzler |
| 5,342,369 A | 8/1994 | Harryman, II |
| 5,350,380 A | 9/1994 | Goble |
| 5,354,300 A | 10/1994 | Goble |
| 5,411,523 A | 5/1995 | Goble |
| 5,417,691 A | 5/1995 | Hayhurst |
| 5,417,701 A | 5/1995 | Holmes |
| 5,439,467 A | 8/1995 | Benderev |
| 5,454,823 A | 10/1995 | Richardson |
| 5,464,427 A | 11/1995 | Curtis |
| 5,466,243 A | 11/1995 | Schmieding |
| 5,480,403 A | 1/1996 | Lee |
| 5,486,197 A | 1/1996 | Le |
| 5,544,664 A | 8/1996 | Benderev |
| 5,545,180 A | 8/1996 | Le |
| 5,562,683 A | 10/1996 | Chan |
| 5,562,684 A | 10/1996 | Kammerer |
| 5,562,687 A | 10/1996 | Chan |
| 5,569,306 A | 10/1996 | Thal |
| 5,572,770 A | 11/1996 | Boden |
| 5,575,801 A | 11/1996 | Habermeyer |
| 5,584,836 A | 12/1996 | Ballintyn |
| 5,584,839 A | 12/1996 | Gieringer |
| 5,601,557 A | 2/1997 | Hayhurst |
| 5,601,562 A | 2/1997 | Wolf |
| 5,620,012 A | 4/1997 | Benderev |
| 5,624,446 A | 4/1997 | Harryman, II |
| 5,630,824 A | 5/1997 | Hart |
| 5,637,112 A | 6/1997 | Moore |
| 5,643,321 A | 7/1997 | McDevitt |
| 5,645,568 A | 7/1997 | Chervitz |
| 5,647,874 A | 7/1997 | Hayhurst |
| 5,649,963 A | 7/1997 | McDevitt |
| 5,658,313 A | 8/1997 | Thal |
| 5,665,112 A | 9/1997 | Thal |
| 5,681,333 A | 10/1997 | Burkhart |
| 5,683,401 A | 11/1997 | Schmieding |
| 5,683,418 A | 11/1997 | Luscombe |
| 5,683,419 A | 11/1997 | Thal |
| 5,688,284 A | 11/1997 | Chervitz |
| 5,690,676 A | 11/1997 | DiPoto |
| 5,690,677 A | 11/1997 | Schmieding |
| 5,700,266 A | 12/1997 | Harryman, II |
| 5,702,397 A | 12/1997 | Goble |
| 5,702,398 A | 12/1997 | Tarabishy |
| 5,709,708 A | 1/1998 | Thal |
| 5,720,765 A | 2/1998 | Thal |
| 5,725,529 A | 3/1998 | Nicholson |
| 5,728,136 A | 3/1998 | Thal |
| 5,730,747 A | 3/1998 | Ek |
| 5,733,307 A | 3/1998 | Dinsdale |
| 5,746,754 A | 5/1998 | Chan |
| 5,746,763 A | 5/1998 | Benderev |
| 5,749,884 A | 5/1998 | Benderev |
| 5,755,728 A | 5/1998 | Maki |
| 5,766,221 A | 6/1998 | Benderev |
| 5,776,151 A | 7/1998 | Chan |
| 5,782,864 A | 7/1998 | Lizardi |
| 5,797,963 A | 8/1998 | McDevitt |
| 5,800,447 A | 9/1998 | Wenstrom, Jr. |
| 5,814,071 A | 9/1998 | McDevitt |
| 5,824,009 A | 10/1998 | Fukuda |
| RE36,020 E | 12/1998 | Moore |
| 5,842,478 A | 12/1998 | Benderev |
| 5,860,978 A | 1/1999 | McDevitt |
| 5,868,762 A | 2/1999 | Cragg |
| 5,891,150 A | 4/1999 | Chan |
| 5,891,168 A | 4/1999 | Thal |
| 5,895,425 A | 4/1999 | Grafton |
| 5,906,624 A | 5/1999 | Wenstrom, Jr. |
| 5,911,721 A | 6/1999 | Nicholson |
| 5,918,604 A | 7/1999 | Whelan |
| 5,935,129 A | 8/1999 | McDevitt |
| 5,938,686 A | 8/1999 | Benderev |
| 5,947,982 A | 9/1999 | Duran |
| 5,948,000 A | 9/1999 | Larsen |
| 5,957,924 A | 9/1999 | Tormala |
| 5,961,530 A | 10/1999 | Moore |
| 5,964,783 A | 10/1999 | Grafton |
| 5,968,044 A | 10/1999 | Nicholson |
| 5,980,558 A | 11/1999 | Wiley |
| 6,001,104 A | 12/1999 | Benderev |
| 6,024,758 A | 2/2000 | Thal |
| 6,029,805 A | 2/2000 | Alpern |
| 6,045,574 A | 4/2000 | Thal |
| 6,086,608 A | 7/2000 | Ek |
| 6,099,538 A | 8/2000 | Moses |
| 6,120,511 A | 9/2000 | Chan |
| 6,132,433 A | 10/2000 | Whelan |
| 6,143,017 A | 11/2000 | Thal |
| 6,156,039 A | 12/2000 | Thal |
| 6,183,479 B1 | 2/2001 | Törmälä |
| 6,267,766 B1 | 7/2001 | Burkhart |
| 6,290,711 B1 | 9/2001 | Caspari |
| 6,302,886 B1 | 10/2001 | McDevitt |
| 6,319,252 B1 | 11/2001 | McDevitt |
| 6,319,269 B1 | 11/2001 | Li |
| 6,368,335 B1 | 4/2002 | Chan |
| 6,371,124 B1 | 4/2002 | Whelan |
| 6,387,129 B2 | 5/2002 | Rieser |
| RE37,963 E | 1/2003 | Thal |
| 6,508,830 B2 | 1/2003 | Steiner |
| 6,511,487 B1 | 1/2003 | Oren |
| 6,514,274 B1 | 2/2003 | Boucher |
| 6,517,546 B2 | 2/2003 | Whittaker |
| 6,520,980 B1 | 2/2003 | Foerster |
| 6,524,316 B1 | 2/2003 | Nicholson |
| 6,524,317 B1 | 2/2003 | Ritchart |
| 6,527,794 B1 | 3/2003 | McDevitt |
| 6,527,795 B1 | 3/2003 | Lizardi |
| 6,537,319 B2 | 3/2003 | Whelan |
| 6,540,750 B2 | 4/2003 | Burkhart |
| 6,544,281 B2 | 4/2003 | ElAttrache |
| 6,547,807 B2 | 4/2003 | Chan |
| 6,585,730 B1 | 7/2003 | Foerster |
| 6,599,295 B1 | 7/2003 | Tornier |
| 6,605,096 B1 | 8/2003 | Ritchart |
| 6,610,064 B1 | 8/2003 | Goble |
| 6,616,674 B2 | 9/2003 | Schmieding |
| 6,623,524 B2 | 9/2003 | Schmieding |
| 6,629,984 B1 | 10/2003 | Chan |
| 6,638,283 B2 | 10/2003 | Thal |
| 6,641,596 B1 | 11/2003 | Lizardi |
| 6,641,597 B2 | 11/2003 | Burkhart |
| 6,645,227 B2 | 11/2003 | Fallin |
| 6,652,561 B1 | 11/2003 | Tran |
| 6,656,182 B1 | 12/2003 | Hayhurst |
| 6,656,183 B2 | 12/2003 | Colleran |
| 6,660,023 B2 | 12/2003 | McDevitt |
| 6,673,094 B1 | 1/2004 | McDevitt |
| 6,692,516 B2 | 2/2004 | West, Jr. |
| 6,712,849 B2 | 3/2004 | Re |
| 6,716,234 B2 | 4/2004 | Grafton |
| 6,723,107 B1 | 4/2004 | Skiba |
| 6,733,506 B1 | 5/2004 | McDevitt |
| 6,733,529 B2 | 5/2004 | Whelan |
| 6,743,233 B1 | 6/2004 | Baldwin |
| 6,770,073 B2 | 8/2004 | McDevitt |
| 6,770,076 B2 | 8/2004 | Foerster |

(56) References Cited

U.S. PATENT DOCUMENTS

| | | |
|---|---|---|
| 6,770,084 B1 | 8/2004 | Bain |
| 6,780,198 B1 | 8/2004 | Gregoire |
| 6,830,572 B2 | 12/2004 | McDevitt |
| 6,855,157 B2 | 2/2005 | Foerster |
| 6,860,887 B1 | 3/2005 | Frankle |
| 6,878,166 B2 | 4/2005 | Clark |
| 6,887,259 B2 | 5/2005 | Lizardi |
| 6,932,826 B2 | 8/2005 | Chan |
| 6,942,683 B2 | 9/2005 | Bonutti |
| 6,955,678 B2 | 10/2005 | Gabriel |
| 6,958,067 B2 | 10/2005 | Whittaker |
| 6,974,477 B2 | 12/2005 | Whelan |
| 6,984,237 B2 | 1/2006 | Hatch |
| 6,986,781 B2 | 1/2006 | Smith |
| 6,991,636 B2 | 1/2006 | Rose |
| 6,994,719 B2 | 2/2006 | Grafton |
| 6,994,725 B1 | 2/2006 | Goble |
| 7,029,490 B2 | 4/2006 | Grafton |
| 7,033,364 B1 | 4/2006 | Walters |
| 7,037,324 B2 | 5/2006 | Martinek |
| 7,063,724 B2 | 6/2006 | Re |
| 7,066,956 B2 | 6/2006 | Schmieding |
| 7,074,203 B1 | 7/2006 | Johanson |
| 7,077,863 B2 | 7/2006 | Schmieding |
| 7,081,126 B2 | 7/2006 | McDevitt |
| 7,083,638 B2 | 8/2006 | Foerster |
| 7,108,700 B2 | 9/2006 | Chan |
| 7,112,208 B2 | 9/2006 | Morris |
| 7,147,651 B2 | 12/2006 | Morrison |
| 7,172,595 B1 | 2/2007 | Goble |
| 7,175,632 B2 | 2/2007 | Singhatat |
| 7,195,642 B2 | 3/2007 | McKernan |
| 7,201,756 B2 | 4/2007 | Ross |
| 7,226,469 B2 | 6/2007 | Benavitz |
| 7,229,448 B2 | 6/2007 | Goble |
| 7,235,100 B2 | 6/2007 | Martinek |
| 7,247,164 B1 | 7/2007 | Ritchart |
| 7,285,124 B2 | 10/2007 | Foerster |
| 7,306,626 B2 | 12/2007 | Whelan |
| 7,309,337 B2 | 12/2007 | Colleran |
| 7,309,346 B2 | 12/2007 | Martinek |
| 7,329,272 B2 | 2/2008 | Burkhart |
| 7,341,592 B1 | 3/2008 | Walters |
| D569,973 S | 5/2008 | Oren |
| 7,377,926 B2 | 5/2008 | Topper |
| 7,381,212 B2 | 6/2008 | Topper |
| 7,381,213 B2 | 6/2008 | Lizardi |
| 7,399,302 B2 | 7/2008 | Goble |
| D576,277 S | 9/2008 | Oren |
| 7,458,975 B2 | 12/2008 | May |
| 7,465,308 B2 | 12/2008 | Sikora |
| 7,500,990 B2 | 3/2009 | Whelan |
| 7,517,357 B2 | 4/2009 | Abrams |
| 7,527,648 B2 | 5/2009 | May |
| 7,530,999 B2 | 5/2009 | Clark |
| 7,556,640 B2 | 7/2009 | Foerster |
| 7,569,059 B2 | 8/2009 | Cerundolo |
| 7,585,305 B2 | 9/2009 | Dreyfuss |
| 7,585,311 B2 | 9/2009 | Green |
| 7,588,587 B2 | 9/2009 | Barbieri |
| 7,588,595 B2 | 9/2009 | Miller |
| 7,594,917 B2 | 9/2009 | Whittaker |
| 7,608,084 B2 | 10/2009 | Oren |
| 7,625,386 B2 | 12/2009 | Abe |
| 7,637,926 B2 | 12/2009 | Foerster |
| 7,651,495 B2 | 1/2010 | McDevitt |
| 7,655,011 B2 | 2/2010 | Whittaker |
| 7,662,171 B2 | 2/2010 | West, Jr. |
| 7,674,275 B2 | 3/2010 | Martin |
| 7,674,290 B2 | 3/2010 | McKernan |
| 7,678,134 B2 | 3/2010 | Schmieding |
| 7,682,374 B2 | 3/2010 | Foerster |
| 7,695,494 B2 | 4/2010 | Foerster |
| 7,713,286 B2 | 5/2010 | Singhatat |
| 7,713,300 B2 | 5/2010 | Meridew |
| 7,749,237 B2 | 7/2010 | Chan |
| 7,771,441 B2 | 8/2010 | Cerundolo |
| 7,803,173 B2 | 9/2010 | Burkhart |
| 7,819,898 B2 | 10/2010 | Stone |
| 7,833,230 B2 | 11/2010 | Cerundolo |
| 7,833,244 B2 | 11/2010 | Cerundolo |
| 7,837,710 B2 | 11/2010 | Lombardo |
| 7,837,718 B2 | 11/2010 | Clark |
| 7,842,050 B2 * | 11/2010 | Diduch ............ A61B 17/0469 606/148 |
| 7,867,264 B2 | 1/2011 | McDevitt |
| 7,868,251 B2 | 1/2011 | Gladd |
| 7,879,046 B2 | 2/2011 | Weinert |
| 7,879,048 B2 | 2/2011 | Bain |
| 7,883,519 B2 | 2/2011 | Oren |
| 7,892,256 B2 | 2/2011 | Grafton |
| 7,896,907 B2 | 3/2011 | McDevitt |
| 7,896,917 B2 | 3/2011 | Walters |
| 7,905,903 B2 | 3/2011 | Stone |
| 7,931,657 B2 | 4/2011 | Walters |
| 7,938,847 B2 | 5/2011 | Fanton |
| 7,942,878 B2 * | 5/2011 | Fernandez ............ A61B 17/82 269/3 |
| 7,942,914 B2 | 5/2011 | Cerundolo |
| 7,955,341 B2 | 6/2011 | Cerundolo |
| 7,959,649 B2 | 6/2011 | Burkhart |
| 7,959,650 B2 | 6/2011 | Kaiser |
| 7,963,972 B2 | 6/2011 | Foerster |
| 7,963,983 B2 | 6/2011 | Cerundolo |
| RE42,526 E | 7/2011 | Reiser |
| 7,976,565 B1 | 7/2011 | Meridew |
| 7,981,140 B2 | 7/2011 | Burkhart |
| 7,988,697 B2 | 8/2011 | Miller |
| 7,993,369 B2 * | 8/2011 | Dreyfuss ............ A61B 17/0401 606/104 |
| 8,012,171 B2 | 9/2011 | Schmieding |
| 8,012,172 B2 | 9/2011 | Grafton |
| 8,012,174 B2 | 9/2011 | ElAttrache |
| 8,029,537 B2 | 10/2011 | West, Jr. |
| 8,038,652 B2 | 10/2011 | Morrison |
| 8,043,308 B2 | 10/2011 | Bittenson |
| 8,062,295 B2 | 11/2011 | McDevitt |
| 8,080,013 B2 | 12/2011 | Whittaker |
| 8,083,769 B2 | 12/2011 | Cauldwell |
| 8,088,146 B2 | 1/2012 | Wert |
| 8,100,942 B1 | 1/2012 | Green |
| 8,105,343 B2 | 1/2012 | White |
| 8,109,966 B2 | 2/2012 | Ritchart |
| 8,109,969 B1 | 2/2012 | Green |
| 8,114,128 B2 | 2/2012 | Cauldwell |
| 8,118,835 B2 | 2/2012 | Weisel |
| 8,128,634 B2 | 3/2012 | Whittaker |
| 8,133,258 B2 | 3/2012 | Foerster |
| 8,137,360 B2 | 3/2012 | Whittaker |
| 8,137,381 B2 | 3/2012 | Foerster |
| 8,137,383 B2 | 3/2012 | West, Jr. |
| 8,147,505 B2 | 4/2012 | Delli-Santi |
| 8,162,978 B2 | 4/2012 | Lombardo |
| 8,167,906 B2 | 5/2012 | Cauldwell |
| 8,177,796 B2 | 5/2012 | Akyuz |
| 8,202,295 B2 | 6/2012 | Kaplan |
| 8,202,296 B2 | 6/2012 | Burkhart |
| 8,202,297 B2 | 6/2012 | Burkhart |
| 8,226,716 B2 | 7/2012 | Mckernan |
| 8,231,653 B2 | 7/2012 | Dreyfuss |
| 8,262,675 B2 | 9/2012 | Cropper |
| 8,267,964 B2 | 9/2012 | Green |
| 8,277,451 B2 * | 10/2012 | Fernandez ............ A61B 17/82 606/103 |
| 8,277,458 B2 | 10/2012 | Schneider |
| 8,277,464 B2 | 10/2012 | Bittenson |
| 8,277,484 B2 | 10/2012 | Barbieri |
| 8,282,643 B2 * | 10/2012 | Dross ................ A61B 17/0483 606/139 |
| 8,282,659 B2 | 10/2012 | Oren |
| 8,298,262 B2 | 10/2012 | Stone |
| 8,317,829 B2 | 11/2012 | Foerster |
| 8,317,862 B2 | 11/2012 | Troger |
| 8,328,843 B2 | 12/2012 | Oren |

(56) References Cited

U.S. PATENT DOCUMENTS

| | | | |
|---|---|---|---|
| 8,348,975 B2 | 1/2013 | Dreyfuss | |
| 8,361,079 B2 | 1/2013 | Pandya | |
| 8,372,124 B2 | 2/2013 | Paulk | |
| 8,382,835 B2 | 2/2013 | Meridew | |
| 8,383,188 B2 | 2/2013 | Mazzocca | |
| 8,388,654 B2* | 3/2013 | Snyder | A61B 17/0401 606/232 |
| 8,394,112 B2 | 3/2013 | Nason | |
| 8,394,123 B2 | 3/2013 | Cauldwell | |
| 8,409,204 B2 | 4/2013 | Martin | |
| 8,409,225 B2* | 4/2013 | Bull | A61B 17/0469 606/148 |
| 8,419,794 B2 | 4/2013 | ElAttrache | |
| 8,425,536 B2 | 4/2013 | Foerster | |
| 8,430,909 B2 | 4/2013 | Dreyfuss | |
| 8,435,264 B2 | 5/2013 | Sojka | |
| 8,444,672 B2 | 5/2013 | Foerster | |
| 8,444,674 B2 | 5/2013 | Kaplan | |
| 8,449,552 B2 | 5/2013 | Sanders | |
| 8,454,654 B2 | 6/2013 | Ferragamo | |
| 8,460,340 B2 | 6/2013 | Sojka | |
| 8,465,521 B2 | 6/2013 | Cook | |
| 8,465,522 B2 | 6/2013 | Burkhart | |
| 8,469,998 B2 | 6/2013 | Sojka | |
| 8,491,595 B2 | 7/2013 | Volpi | |
| 8,491,600 B2 | 7/2013 | McDevitt | |
| 8,506,596 B2 | 8/2013 | Stone | |
| 8,512,378 B2 | 8/2013 | Green | |
| 8,518,091 B2 | 8/2013 | McDevitt | |
| 8,523,902 B2 | 9/2013 | Heaven | |
| 8,529,577 B2 | 9/2013 | Hirt | |
| 8,529,601 B2 | 9/2013 | Green | |
| 8,535,350 B2 | 9/2013 | Lizardi | |
| 8,540,732 B2 | 9/2013 | Weinert | |
| 8,540,737 B2 | 9/2013 | Chudik | |
| 8,551,123 B2 | 10/2013 | Pandya | |
| 8,556,911 B2 | 10/2013 | Mehta | |
| 8,579,974 B2 | 11/2013 | Pandya | |
| 8,591,580 B2 | 11/2013 | Mckernan | |
| 8,597,328 B2 | 12/2013 | Cauldwell | |
| 8,613,756 B2 | 12/2013 | Lizardi | |
| 8,617,186 B2 | 12/2013 | White | |
| 8,617,219 B2 | 12/2013 | Oren | |
| 8,623,032 B2 | 1/2014 | Diduch | |
| 8,652,171 B2 | 2/2014 | Stone | |
| 8,657,854 B2 | 2/2014 | Foerster | |
| 8,663,279 B2* | 3/2014 | Burkhart | A61B 17/0401 606/232 |
| 8,663,280 B2 | 3/2014 | Kaplan | |
| 8,672,954 B2 | 3/2014 | Oren | |
| 8,672,966 B2 | 3/2014 | Wert | |
| 8,672,967 B2 | 3/2014 | DiMatteo | |
| 8,672,970 B2 | 3/2014 | Ferragamo | |
| 8,685,060 B2 | 4/2014 | Foerster | |
| 8,690,915 B2 | 4/2014 | Hootstein | |
| 8,696,688 B2 | 4/2014 | Stone | |
| 8,702,752 B2 | 4/2014 | Schmieding | |
| 8,702,754 B2 | 4/2014 | DiMatteo | |
| 8,709,040 B2 | 4/2014 | Anderhub | |
| 8,709,395 B2 | 4/2014 | Boutros | |
| 8,721,650 B2 | 5/2014 | Fanton | |
| 8,740,913 B2 | 6/2014 | Schneider | |
| 8,747,469 B2 | 6/2014 | Wang | |
| 8,764,798 B2 | 7/2014 | Housman | |
| 8,771,315 B2 | 7/2014 | Lunn | |
| 8,771,351 B2 | 7/2014 | ElAttrache | |
| 8,777,990 B2 | 7/2014 | van der Burg | |
| 8,784,449 B2 | 7/2014 | Snyder | |
| 8,784,489 B2 | 7/2014 | Walters | |
| 8,790,370 B2 | 7/2014 | Spenciner | |
| 8,808,326 B2 | 8/2014 | Gagliano | |
| 8,814,905 B2 | 8/2014 | Sengun | |
| 8,828,029 B2 | 9/2014 | White | |
| 8,834,495 B2 | 9/2014 | White | |
| 8,834,521 B2 | 9/2014 | Pinto | |
| 8,834,543 B2 | 9/2014 | McDevitt | |
| 8,858,560 B2 | 10/2014 | Bradley | |
| 8,870,877 B2 | 10/2014 | Koogle, Jr. | |
| 8,881,635 B2 | 11/2014 | Martin | |
| 8,882,801 B2 | 11/2014 | DiMatteo | |
| 8,906,060 B2 | 12/2014 | Hart | |
| 8,926,663 B2 | 1/2015 | Green | |
| 8,936,620 B2 | 1/2015 | Kaiser | |
| 8,943,941 B2 | 2/2015 | Dow | |
| 8,951,292 B2 | 2/2015 | Paulk | |
| 8,961,576 B2 | 2/2015 | Hodge | |
| 8,986,345 B2 | 3/2015 | Denham | |
| 8,986,346 B2 | 3/2015 | Dreyfuss | |
| 8,986,347 B2 | 3/2015 | Housman | |
| 8,992,573 B2 | 3/2015 | Van Der Burg | |
| 9,005,246 B2 | 4/2015 | Burkhart | |
| 9,017,381 B2 | 4/2015 | Kaiser | |
| 9,023,083 B2 | 5/2015 | Foerster | |
| 9,034,014 B2 | 5/2015 | Catania | |
| 9,044,222 B2 | 6/2015 | Dross | |
| 9,044,226 B2 | 6/2015 | Green | |
| 9,107,653 B2 | 8/2015 | Sullivan | |
| 9,113,859 B2 | 8/2015 | Dooney, Jr. | |
| 9,144,425 B2 | 9/2015 | Kaplan | |
| 9,149,268 B2 | 10/2015 | Graul | |
| 9,155,542 B2 | 10/2015 | Markarian | |
| 9,161,750 B2 | 10/2015 | Zirps | |
| 9,179,907 B2 | 11/2015 | ElAttrache | |
| 9,198,649 B2 | 12/2015 | Karapetian | |
| 9,226,742 B2 | 1/2016 | Wolf | |
| 9,265,496 B2 | 2/2016 | Sojka | |
| 9,445,805 B2 | 9/2016 | Snell | |
| 9,498,232 B2* | 11/2016 | Perez III | A61B 17/1714 |
| 2001/0016747 A1 | 8/2001 | Romano | |
| 2002/0029066 A1 | 3/2002 | Foerster | |
| 2002/0065526 A1 | 5/2002 | Oren | |
| 2003/0105524 A1 | 6/2003 | Paulos | |
| 2003/0171778 A1 | 9/2003 | Lizardi | |
| 2003/0195528 A1 | 10/2003 | Ritchart | |
| 2003/0195563 A1 | 10/2003 | Foerster | |
| 2003/0229362 A1 | 12/2003 | Chan | |
| 2004/0010286 A1 | 1/2004 | Gieringer | |
| 2004/0082956 A1 | 4/2004 | Baldwin | |
| 2004/0088004 A1 | 5/2004 | Rosch | |
| 2004/0098051 A1 | 5/2004 | Fallin | |
| 2004/0098053 A1 | 5/2004 | Tran | |
| 2004/0116843 A1 | 6/2004 | Chan | |
| 2004/0172062 A1 | 9/2004 | Burkhart | |
| 2004/0267317 A1 | 12/2004 | Higgins | |
| 2005/0033362 A1 | 2/2005 | Grafton | |
| 2005/0033364 A1 | 2/2005 | Gregoire | |
| 2005/0149122 A1 | 7/2005 | McDevitt | |
| 2005/0245932 A1 | 11/2005 | Fanton | |
| 2005/0277986 A1 | 12/2005 | Foerster | |
| 2006/0074438 A1 | 4/2006 | Chan | |
| 2006/0079904 A1 | 4/2006 | Thal | |
| 2006/0142784 A1 | 6/2006 | Kontos | |
| 2006/0149258 A1 | 7/2006 | Sousa | |
| 2006/0155328 A1 | 7/2006 | Foerster | |
| 2006/0241658 A1 | 10/2006 | Cerundolo | |
| 2006/0247641 A1 | 11/2006 | Re | |
| 2006/0271060 A1 | 11/2006 | Gordon | |
| 2006/0282081 A1 | 12/2006 | Fanton | |
| 2006/0282082 A1 | 12/2006 | Fanton | |
| 2006/0282083 A1 | 12/2006 | Fanton | |
| 2006/0293691 A1* | 12/2006 | Mitra | A61B 17/8861 606/103 |
| 2007/0005067 A1 | 1/2007 | Dross | |
| 2007/0005068 A1 | 1/2007 | Sklar | |
| 2007/0016251 A1 | 1/2007 | Roby | |
| 2007/0021751 A1 | 1/2007 | Reay Young | |
| 2007/0027475 A1 | 2/2007 | Pagedas | |
| 2007/0043377 A1* | 2/2007 | Fernandez | A61B 17/82 606/103 |
| 2007/0088362 A1 | 4/2007 | Bonutti | |
| 2007/0156149 A1 | 7/2007 | Fanton | |
| 2007/0156150 A1 | 7/2007 | Fanton | |
| 2007/0156176 A1 | 7/2007 | Fanton | |
| 2007/0167950 A1 | 7/2007 | Tauro | |

(56) References Cited

U.S. PATENT DOCUMENTS

| | | |
|---|---|---|
| 2007/0173845 A1 | 7/2007 | Kim |
| 2007/0203498 A1 | 8/2007 | Gerber |
| 2007/0213730 A1 | 9/2007 | Martinek |
| 2007/0213770 A1 | 9/2007 | Dreyfuss |
| 2007/0219557 A1 | 9/2007 | Bourque |
| 2007/0219558 A1 | 9/2007 | Deutsch |
| 2007/0288023 A1 | 12/2007 | Pellegrino |
| 2008/0009904 A1 | 1/2008 | Bourque |
| 2008/0033486 A1 | 2/2008 | Whittaker |
| 2008/0057838 A1 | 3/2008 | Huang |
| 2008/0077161 A1 | 3/2008 | Kaplan |
| 2008/0103528 A1 | 5/2008 | Zirps |
| 2008/0125815 A1 | 5/2008 | Heaven |
| 2008/0188936 A1 | 8/2008 | Ball |
| 2008/0208253 A1 | 8/2008 | Dreyfuss |
| 2008/0234730 A1 | 9/2008 | Cotton |
| 2008/0243174 A1 | 10/2008 | Oren |
| 2008/0243177 A1 | 10/2008 | Oren |
| 2008/0243178 A1 | 10/2008 | Oren |
| 2008/0275453 A1 | 11/2008 | Lafosse |
| 2008/0287992 A1 | 11/2008 | Tornier |
| 2008/0300629 A1 | 12/2008 | Surti |
| 2009/0018561 A1 | 1/2009 | Schwartz |
| 2009/0018581 A1 | 1/2009 | Anderson |
| 2009/0036905 A1 | 2/2009 | Schmieding |
| 2009/0048623 A1 | 2/2009 | Lafosse |
| 2009/0062819 A1 | 3/2009 | Burkhart |
| 2009/0076544 A1 | 3/2009 | DiMatteo |
| 2009/0099598 A1 | 4/2009 | McDevitt |
| 2009/0138002 A1 | 5/2009 | Fenton |
| 2009/0149884 A1 | 6/2009 | Snyder |
| 2009/0171360 A1 | 7/2009 | Whelan |
| 2009/0187216 A1 | 7/2009 | Schmieding |
| 2009/0192546 A1 | 7/2009 | Schmieding |
| 2009/0222039 A1 | 9/2009 | Dreyfuss |
| 2009/0287246 A1 | 11/2009 | Cauldwell |
| 2009/0292313 A1 | 11/2009 | Anspach, III |
| 2009/0312782 A1 | 12/2009 | Park |
| 2009/0312794 A1 | 12/2009 | Nason |
| 2009/0318960 A1 | 12/2009 | Burkhart |
| 2010/0004683 A1 | 1/2010 | Hoof |
| 2010/0087872 A1 | 4/2010 | Morihara |
| 2010/0100129 A1 | 4/2010 | West, Jr. |
| 2010/0121337 A1 | 5/2010 | Pandya |
| 2010/0121348 A1 | 5/2010 | van der Burg |
| 2010/0121354 A1* | 5/2010 | Pandya ............ A61B 17/1714 606/148 |
| 2010/0121375 A1* | 5/2010 | Pandya ............ A61B 17/1714 606/232 |
| 2010/0121447 A1* | 5/2010 | Troger ............. A61B 17/1764 623/13.11 |
| 2010/0137889 A1 | 6/2010 | Oren |
| 2010/0179573 A1 | 7/2010 | Levinsohn |
| 2010/0198235 A1 | 8/2010 | Pierce |
| 2010/0249835 A1 | 9/2010 | Schwartz |
| 2010/0262184 A1 | 10/2010 | Dreyfuss |
| 2010/0318125 A1 | 12/2010 | Gerber |
| 2010/0318139 A1 | 12/2010 | Beauchamp |
| 2010/0324575 A1 | 12/2010 | Chan |
| 2011/0009867 A1* | 1/2011 | Oren ................. A61B 17/0482 606/80 |
| 2011/0009884 A1 | 1/2011 | Kaplan |
| 2011/0022087 A1 | 1/2011 | Cerundolo |
| 2011/0028997 A1 | 2/2011 | Gregoire |
| 2011/0071550 A1 | 3/2011 | Diduch |
| 2011/0106013 A1 | 5/2011 | Whittaker |
| 2011/0106124 A1* | 5/2011 | Beauchamp ....... A61B 17/0482 606/170 |
| 2011/0112550 A1 | 5/2011 | Heaven |
| 2011/0112576 A1 | 5/2011 | Nguyen |
| 2011/0118757 A1 | 5/2011 | Pierce |
| 2011/0118762 A1 | 5/2011 | Dooney, Jr. |
| 2011/0152928 A1 | 6/2011 | Colleran |
| 2011/0190815 A1 | 8/2011 | Saliman |
| 2011/0208198 A1* | 8/2011 | Anderson ......... A61B 17/1739 606/87 |
| 2011/0224726 A1 | 9/2011 | Lombardo |
| 2011/0238111 A1 | 9/2011 | Frank |
| 2011/0238112 A1 | 9/2011 | Kim |
| 2011/0238113 A1 | 9/2011 | Fanton |
| 2011/0245869 A1 | 10/2011 | Burkhart |
| 2011/0301622 A1 | 12/2011 | Oren |
| 2012/0041484 A1 | 2/2012 | Briganti |
| 2012/0059415 A1 | 3/2012 | Sklar |
| 2012/0116451 A1 | 5/2012 | Tepic |
| 2012/0143224 A1 | 6/2012 | Chan |
| 2012/0150225 A1 | 6/2012 | Burkhart |
| 2012/0150235 A1 | 6/2012 | Snyder |
| 2012/0158051 A1 | 6/2012 | Foerster |
| 2012/0165868 A1 | 6/2012 | Burkhart |
| 2012/0179200 A1 | 7/2012 | Cauldwell |
| 2012/0197296 A1 | 8/2012 | Mayer |
| 2012/0209279 A1* | 8/2012 | Snyder ............... A61B 17/0401 606/103 |
| 2012/0209325 A1 | 8/2012 | Gagliano |
| 2012/0245634 A1 | 9/2012 | Kaplan |
| 2012/0265219 A1* | 10/2012 | Rushdy ............. A61B 17/0401 606/139 |
| 2012/0272816 A1 | 11/2012 | Ueda |
| 2013/0023928 A1 | 1/2013 | Dreyfuss |
| 2013/0023929 A1 | 1/2013 | Sullivan |
| 2013/0023930 A1 | 1/2013 | Stone |
| 2013/0035720 A1 | 2/2013 | Perriello |
| 2013/0053959 A1* | 2/2013 | Lizardi .............. A61B 17/1714 623/13.14 |
| 2013/0060280 A1* | 3/2013 | Wolf ................. A61B 17/0401 606/232 |
| 2013/0096611 A1 | 4/2013 | Sullivan |
| 2013/0103083 A1 | 4/2013 | Baird |
| 2013/0123809 A1 | 5/2013 | Murphy |
| 2013/0123840 A1* | 5/2013 | Murphy ............. A61B 17/0469 606/228 |
| 2013/0123842 A1 | 5/2013 | Chan |
| 2013/0123843 A1 | 5/2013 | Chan |
| 2013/0144335 A1 | 6/2013 | Sandow |
| 2013/0150885 A1 | 6/2013 | Dreyfuss |
| 2013/0165972 A1 | 6/2013 | Sullivan |
| 2013/0178854 A1* | 7/2013 | Sholev ............... A61B 17/0469 606/79 |
| 2013/0190782 A1 | 7/2013 | Nason |
| 2013/0190871 A1 | 7/2013 | Markarian |
| 2013/0197575 A1 | 8/2013 | Karapetian |
| 2013/0197577 A1 | 8/2013 | Wolf |
| 2013/0197578 A1 | 8/2013 | Gregoire |
| 2013/0204253 A1 | 8/2013 | Oren |
| 2013/0204299 A1 | 8/2013 | Mantovani |
| 2013/0211429 A1 | 8/2013 | Snyder |
| 2013/0218273 A1 | 8/2013 | Bull |
| 2013/0226231 A1 | 8/2013 | Weinert |
| 2013/0267998 A1* | 10/2013 | Vijay ................. A61B 17/0401 606/232 |
| 2013/0296936 A1 | 11/2013 | Burkhart |
| 2013/0325011 A1* | 12/2013 | Cleveland .......... A61B 17/0482 606/80 |
| 2013/0338710 A1 | 12/2013 | Heaven |
| 2013/0345711 A1 | 12/2013 | Mehta |
| 2013/0345749 A1 | 12/2013 | Sullivan |
| 2013/0345750 A1* | 12/2013 | Sullivan ............ A61B 17/0401 606/232 |
| 2014/0046369 A1 | 2/2014 | Heaven |
| 2014/0046443 A1 | 2/2014 | Mckernan |
| 2014/0081320 A1 | 3/2014 | Sengun |
| 2014/0107700 A1* | 4/2014 | Baird ................. A61B 17/0401 606/232 |
| 2014/0114317 A1 | 4/2014 | Oren |
| 2014/0114411 A1 | 4/2014 | Baird |
| 2014/0121467 A1 | 5/2014 | Vayser |
| 2014/0134802 A1 | 5/2014 | Lin |
| 2014/0135802 A1 | 5/2014 | Mantovani |
| 2014/0163612 A1 | 6/2014 | Hootstein |
| 2014/0171948 A1* | 6/2014 | Griffiths ............ A61B 17/1637 606/80 |

(56) References Cited

U.S. PATENT DOCUMENTS

| | | | |
|---|---|---|---|
| 2014/0172016 A1 | 6/2014 | Housman | |
| 2014/0186416 A1 | 7/2014 | Boutros | |
| 2014/0186418 A1 | 7/2014 | Boutros | |
| 2014/0194906 A1 | 7/2014 | Topper | |
| 2014/0207189 A1 | 7/2014 | Foerster | |
| 2014/0214038 A1* | 7/2014 | Sholev | A61B 17/0483 606/79 |
| 2014/0222072 A1 | 8/2014 | Gerber | |
| 2014/0243892 A1 | 8/2014 | Choinski | |
| 2014/0257384 A1 | 9/2014 | Dreyfuss | |
| 2014/0288594 A1 | 9/2014 | Shaefers | |
| 2014/0303625 A1* | 10/2014 | Sholev | A61B 17/0482 606/80 |
| 2014/0324100 A1 | 10/2014 | Burkhart | |
| 2014/0343605 A1 | 11/2014 | Lunn | |
| 2014/0364876 A1 | 12/2014 | White | |
| 2014/0364905 A1 | 12/2014 | Lunn | |
| 2014/0364907 A1 | 12/2014 | White | |
| 2014/0379027 A1 | 12/2014 | Dreyfuss | |
| 2014/0379028 A1 | 12/2014 | Lo | |
| 2015/0005773 A1 | 1/2015 | Oren | |
| 2015/0005817 A1 | 1/2015 | Snyder | |
| 2015/0005818 A1 | 1/2015 | McDevitt | |
| 2015/0025552 A1 | 1/2015 | Stoll | |
| 2015/0032155 A1 | 1/2015 | Dreyfuss | |
| 2015/0032157 A1 | 1/2015 | Dooney, Jr. | |
| 2015/0045795 A1* | 2/2015 | Sholev | A61B 17/0469 606/79 |
| 2015/0051645 A1 | 2/2015 | Green | |
| 2015/0066079 A1 | 3/2015 | Schmieding | |
| 2015/0066080 A1 | 3/2015 | Olson | |
| 2015/0066081 A1 | 3/2015 | Martin | |
| 2015/0088196 A1 | 3/2015 | Kaplan | |
| 2015/0119937 A1 | 4/2015 | Lunn | |
| 2015/0141998 A1 | 5/2015 | Kiapour | |
| 2015/0150551 A1 | 6/2015 | Paulk | |
| 2015/0157312 A1 | 6/2015 | Burkhart | |
| 2015/0196388 A1* | 7/2015 | Housman | A61B 17/0401 606/304 |
| 2015/0216522 A1 | 8/2015 | Ticker | |
| 2015/0223926 A1 | 8/2015 | Foerster | |
| 2015/0245831 A1 | 9/2015 | Sullivan | |
| 2015/0297211 A1 | 10/2015 | Sullivan | |
| 2015/0297274 A1 | 10/2015 | Dreyfuss | |
| 2015/0313586 A1 | 11/2015 | Burkhart | |
| 2015/0327849 A1 | 11/2015 | Dooney, Jr. | |
| 2015/0335327 A1 | 11/2015 | Ferguson | |
| 2015/0351752 A1 | 12/2015 | Rousseau | |
| 2015/0359533 A1 | 12/2015 | Kaplan | |
| 2016/0015380 A1* | 1/2016 | Sholev | A61B 17/0482 606/80 |
| 2016/0296224 A1 | 10/2016 | Snell | |
| 2016/0338689 A1 | 11/2016 | Baird | |
| 2016/0338693 A1 | 11/2016 | Graul | |
| 2017/0100182 A1* | 4/2017 | Shah | A61B 17/8872 |

FOREIGN PATENT DOCUMENTS

| | | |
|---|---|---|
| WO | WO2004049958 A1 | 6/2004 |
| WO | WO2009018565 A1 | 2/2009 |
| WO | WO2009042951 A1 | 4/2009 |
| WO | WO2009055800 A1 | 4/2009 |
| WO | WO2009076526 A1 | 6/2009 |
| WO | WO2010005749 A1 | 1/2010 |
| WO | WO2010009217 A1 | 1/2010 |
| WO | WO2010056786 A2 | 5/2010 |
| WO | WO2010056787 A2 | 5/2010 |
| WO | WO2011056701 A1 | 5/2011 |
| WO | WO2011059995 A2 | 5/2011 |
| WO | WO2011060022 A2 | 5/2011 |
| WO | WO2011060437 A1 | 5/2011 |
| WO | WO2011133233 A1 | 10/2011 |
| WO | WO2012024446 A2 | 2/2012 |
| WO | WO2012052891 A1 | 4/2012 |
| WO | WO2012129388 A1 | 9/2012 |
| WO | WO2013014553 A1 | 1/2013 |
| WO | WO2013027210 A1 | 2/2013 |
| WO | WO2013052128 A1 | 4/2013 |
| WO | WO2013112449 A1 | 8/2013 |
| WO | WO2013151817 A1 | 10/2013 |
| WO | WO2013181212 A1 | 12/2013 |
| WO | WO2014051930 A2 | 4/2014 |
| WO | WO2014055678 A1 | 4/2014 |
| WO | WO2014059378 A1 | 4/2014 |
| WO | WO2014066116 A1 | 5/2014 |
| WO | WO2014071052 A1 | 5/2014 |
| WO | WO2014071066 A1 | 5/2014 |
| WO | WO2014018946 A9 | 12/2014 |
| WO | WO2015005951 A1 | 1/2015 |
| WO | WO2015008176 A2 | 1/2015 |
| WO | WO2015017426 A1 | 2/2015 |
| WO | WO2015031559 A1 | 3/2015 |
| WO | WO2016148941 A1 | 9/2016 |

OTHER PUBLICATIONS

Carter, Sally L., et al, "Suture Performance in Standard Arthroscopic Knots—Effects of Material and Design" Smith & Nephew, Inc., www.smith-nephew.com, 2004, 4 pp.

OPUS AutoCuff Magnum X Knotless Fixation Implant with Independent Tensioning, ArthroCare Sports Medicine, www.arthrocaresportsmedicine.com, 2009, 2 pp.

The OPUS AutoCuff System for Rotatpr Cuff Repair, ArthroCare Sports Medicine, www.arthrocaresportsmedicine.com, 2006, 8 pp.

The OPUS TwinLock Knotless Fixation System, ArthroCare Sports Medicine, www.arthrocaresportsmedicine.com, 2010, 2 pp.

BioRaptor Knotless Suture Anchor, Smith & Nephew, Inc., www.smith-nephew.com, 2010, 6 pp.

Arthroscopic Shoulder Repair Using the Smith & Nephew Footpring PK Suture Anchor, Smith & Nephew, Inc., www.smith-nephew.com, 2008, 12 pp.

Dr. S. D. Gerber Double Row Method Surgical Technique, Stryker Corporation, www.stryker.com, 2010, 12 pp.

Multifix's PEEK 5.5mm and 6.5mm Knotless Implants Technique Guide, ArthroCare Corporation, www.smith-nephew.com, 2015, 8 pp.

The Fully Threaded Family of Soft Tissue Repair Anchors, Arthrex, Inc., www.arthrex.com, 2012, 6 pp.

2.5 mm PushLock Knotless Suture Anchor, Arthrex, Inc., www.arthrex.com, 2013, 2 pp.

Achilles SpeedBridge Surgical Technique, Arthrex, Inc., www.arthrex.com, 2013, 6 pp.

Biceps Tenodesis SwiveLock System Surgical Technique, Arthrex, Inc., www.arthrex.com, 2012, 6 pp.

Revolutionizing Orthopedic Surgery, FiberWire Braided Composite Suture, Arthrex, Inc., www.arthrex.com, 2012, 8 pp.

Massive Rotator Cuff Repair and Augmentation using the SpeedBridge and ArthroFlex Dermal Matrix Surgical Technique, Arthrex, Inc., www.arthrex.com, 2012, 4 pp.

Arthrex SpeedBridge and Tornier Arthro Tunneler Biomechanical Cadavar Testing, Arthrex, Inc., 2010, 2 pp.

SpeedBridge and SpeedFix Knotless Rotator Cuff Repair using the SwiveLock C and FiberTape Surgical Technique, Arthrex, Inc., www.arthrex.com, 2013, 8 pp.

Double Row Rotator Cuff Repair using the Bio-Corkscrew FT Surgical Technique, Arthrex, Inc. www.arthrex.com, 2007, 6 pp.

SutureBridge Double Row Rotator Cuff Repair Surgical Technique, Arthrex, Inc., www.arthrex.com, 2013, 6 pp.

SwiveLock and FiberChain Knotless Rotator Cuff Repair Surgical Technique, Arthrex, Inc, www.arthrex.com, 2011, 8 pp.

The Next Generation in Shoulder & Elbow Repair and Reconstruction Technology, Arthrex, Inc., www.arthrex.com, 2014, 56 pp.

The Next Generation in Shoulder & Elbow Repair and Reconstruction Technology, Arthrex, Inc., www.arthrex.com, 2015, 56 pp.

Achilles SutureBridge Surgical Technique, Arthrex, Inc., www.arthrex.com, 2014, 6 pp.

Arthrex is Reaching New Heights in Rotator Cuff Repair, Arthrex, Inc., www.arthrex.com, 2007, 8 pp.

(56) References Cited

OTHER PUBLICATIONS

Quattro Shoulder System—Innovative Rotator Cuff Solutions, Cayenne Medical, Inc., www.cayennemedical.com, 6 pp.
Chu, T., et al., "Biomechanical Evaluation of Knotless Fixation Systems for Rotator Cuff Repairs", 56$^{th}$ Annual Meeting of the Orthopaedic Research Society, Post No. 1791, 1 pp.
Flores, Steve, "Comparison of the Pull-Back Effect of Rotator Cuff Anchors", Arthrex, Inc., 2007, 2 pp.
Shoulder Restoration System, PopLok Knotless Suture Anchor, ConMed Linvatec, www.linvatec.com, 8 pp.
Shoulder Restoration System, ConMed Linvatec, www.linvatec.com, 2014, 20 pp.
Shoulder Restoration System, PopLok Knotless Suture Anchor, ConMed Linvatec, www.linvatec.com, 8 pp.
Defranco, Michael J., et al., "Arthroscopic Rotator Cuff Repair Failure Resulting from Decorticiation of the Rotator Cuff Footprint: A Case Report", The American Journal of Orthopedics, Dec. 2009, pp. 32-33.
Halbrecht, Jeffrey, "Versalok a New Technique for Arthroscopic Knotless Rotator Cuff Repair", 44 pp.
Versalok, The Next Generation in Rotator Cuff Repair, DePuy Mitek, 15 pp.
Introducing the HEALIX Advance Family of Suture Anchors, DePuy Mitek, Inc, 2012, 4 pp.
Versalok PEEK, The New, 100% Radiolucent, Self-Punching, Knotless Anchor, DePuy Mitek, Inc., 2010, 4 pp.
The Next Generation in Rotator Cuff Repair, DePuy Mitek, Inc., 2007, 18 pp.
Efird, Chad, et al., "Knotless Single-Row Rotator Cuff Repair: A Comparative Biomechanical Study of 2 Knotless Suture Anchors", Healio.com/Orthopedics, Aug. 2013, 5 pp.
Arthroscopic Shoulder Repair Using the Smith & Nephew Footprint PK Suture Anchor, Smith & Nephew, Inc., 2008, 12 pp.
Knotless SutureTak Instability Repair Surgical Technique, Arthrex, Inc., www.arthrex.com, 2015, 6 pp.
Mall, Nathan A., et al., "Transosseous-Equivalent Rotator Cuff Repair: A Systematic Review on the Biomechanical Importance of Tying the Medial Row", Arthroscopy: The Journal of Arthroscopic and Related Surgery, vol. 29, No. 2, Feb. 2013, pp. 377-386.
Surgical Technique Sharc-FT and Taylor Stitcher Transosseus Devices for Fast Rotator Cuff Repair, NCS Lab Medical Devices Factory, 12 pp.
Nho, Shane J., et al,. "Bioabsorbable Anchors in Glenohumeral Shoulder Surgery", Arthrscopy: The Journal of Arthroscopic and Related Surgery, vol. 25, No. 7, Jul. 2009, pp. 788-793.
CinchLock SS (Sports Sheath) Knotless Labrum Restoration, Stryker Corporation, www.stryker.com, 6 pp.
ReelX STT Knotless Anchor System, Stryker Corporation, www.stryker.com, 2010, 4 pp.
ArthroTunneler TunnelPro System, Transosseous Rotator Cuff Repair, Tornier, Inc., www.tornier.com, 2012, 6 pp.
Pull-Out Strength Comparison of Arthrex to Mitek Suture Anchors, Arthrex Research and Development, Arthrex, Inc., 2010, 1 pp.
Quickdraw Knotless Suture Anchor System Surgical Technique, Writght Medical Technology, Inc. www.wmt.com, 2011, 28 pp.
The DoublePlay Biocomposite Suture Anchor, ArthroCare Sports Medicine, www.arthrocaresportsmedicine.com, 2009, 12 pp.
ALLThread Knotless Suture Anchor, Double Row Rotator Cuff Repair, Biomet Orthopedics, www.biomet.com, 2012, 12 pp.
Arthroscopic and Mini-Open Rotator Cuff Repair Using JuggerKnot Soft Anchor—2.9 mm with ALLthread Knotless Anchor Surgical Technique, Biomet Sports Medicine, www.biomet.com, 2013, 16 pp.

\* cited by examiner

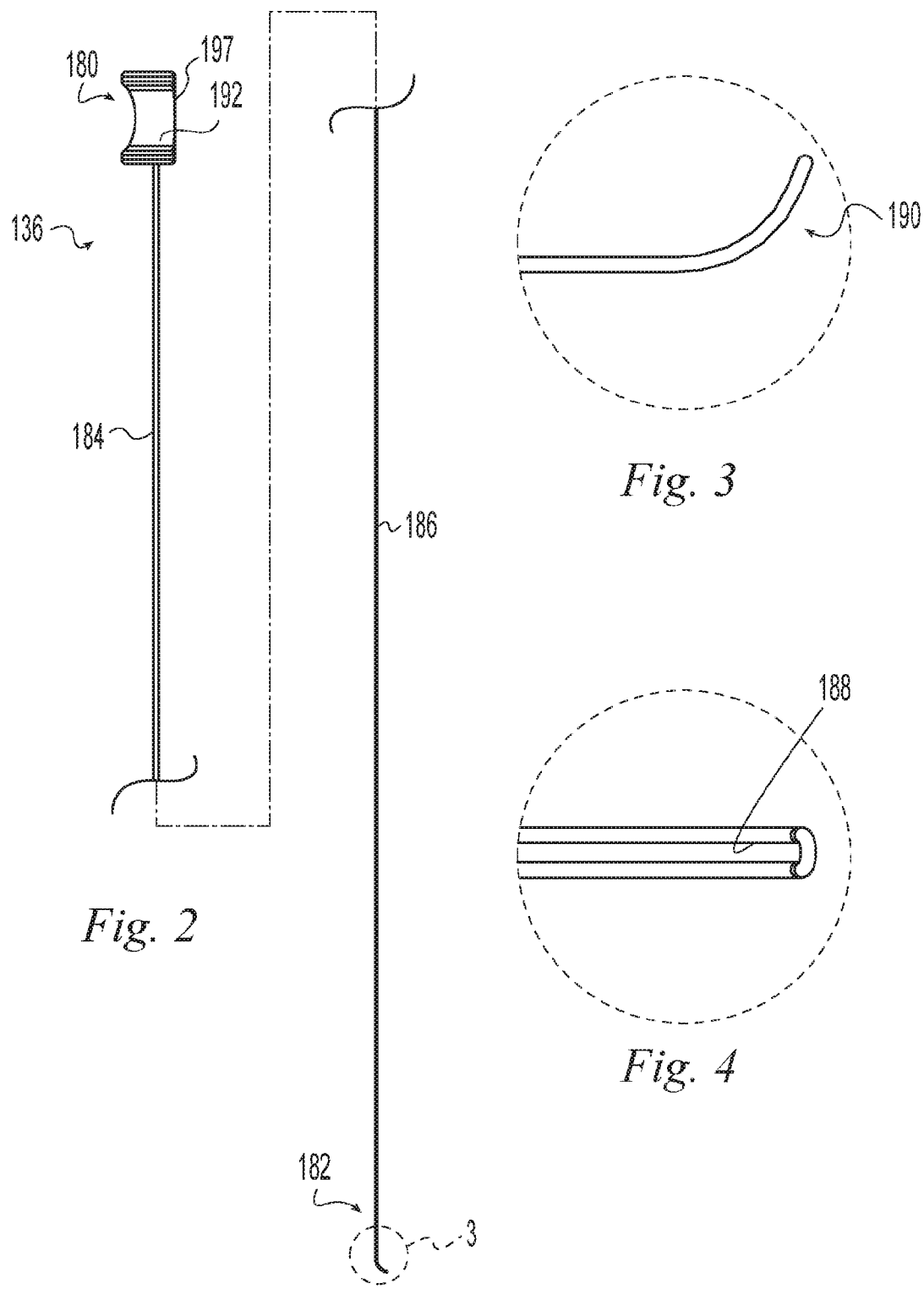

TRANSOSSEOUS GUIDE

CROSS-REFERENCE TO RELATED APPLICATIONS

This application claims the benefit of U.S. Provisional Application No. 62/193,888, filed Jul. 17, 2015, which is hereby incorporated by reference.

FIELD OF THE INVENTION

The invention relates to transosseous guides and methods for transosseous attachments.

BACKGROUND

A variety of surgical procedures require the attachment of something relative to a surgical site. For example, in surgery relating to the skeletal system, it is often advantageous to attach soft tissue, suture, implants, and/or other items in or adjacent to a joint. For example, soft tissues such as ligaments, tendons, fascia, other capsular material, and/or muscle may be attached to an adjacent bone. Such soft tissues may be adjacent to bones at skeletal joints including but not limited to the joints of the hands and feet, ankle, wrist, knee, elbow, hip, shoulder, and spine. For example, it is often advantageous to pass a suture through a portion of a bone to form a transosseous attachment to the bone.

SUMMARY

Examples of the invention provide instruments and methods for surgical transosseous attachment to a bone.

In one example of the invention, a method for placing a member transosseously through first and second transverse, intersecting bone tunnels includes inserting a first tunnel member into a bone along a first insertion axis, the first tunnel member having a proximal end and a distal end, the first tunnel member having a first longitudinal passage at least partway through the first tunnel member; inserting a second tunnel member into the bone along a second insertion axis, the second insertion axis intersecting the first insertion axis, the second tunnel member having a proximal end and a distal end, the second tunnel member having a second longitudinal passage at least partway through the second tunnel member; inserting a passer through the first and second tunnel members, the passer simultaneously extending through the first and second axial passages and out of the proximal end of the first tunnel member and out of the proximal end of the second tunnel member.

In another example of the invention a method for placing suture transosseously through first, second, and third transverse, intersecting bone tunnels includes forming a first bone tunnel in a bone with a first tunnel member; forming a second bone tunnel transverse to and intersecting the first bone tunnel with a second tunnel member; placing a first portion of suture through the first and second bone tunnels and at least partway through the first tunnel member; forming a third bone tunnel transverse to and intersecting the first bone tunnel with the second tunnel member while the first flexible element is present in the first tunnel member; placing a second portion of suture through the first and third tunnels and at least partway through the first tunnel member while the first flexible element is present in the first tunnel member.

In another example of the invention, a method for placing a member transosseously through first and second transverse, intersecting bone tunnels includes inserting a first tunnel member into a bone along a first insertion axis, the first tunnel member having a proximal end and a distal end, the first tunnel member having a first longitudinal passage at least partway through the first tunnel member; using a guide to select a second insertion axis from a plurality of insertion axes that each intersect the first insertion axis, each of the plurality of insertion axes forming a different angle relative to the first insertion axis; inserting a second tunnel member into the bone along the selected second insertion axis, the second tunnel member having a proximal end and a distal end, the second tunnel member having a second longitudinal passage at least partway through the second tunnel member; inserting a passer through the first and second tunnel members, the passer simultaneously extending through the first and second axial passages and out of the proximal end of the first tunnel member and out of the proximal end of the second tunnel member.

BRIEF DESCRIPTION OF THE DRAWINGS

Various examples of the present invention will be discussed with reference to the appended drawings. These drawings depict only illustrative examples of the invention and are not to be considered limiting of its scope.

FIG. 2 is a side elevation view of an example of a passer used with the instrument of FIG. 1;

FIG. 3 is a detail side elevation view of the tip of the passer of FIG. 2;

FIG. 4 is a detail front elevation view of the tip of the passer of FIG. 2;

DESCRIPTION OF THE ILLUSTRATIVE EXAMPLES

Figure 1:
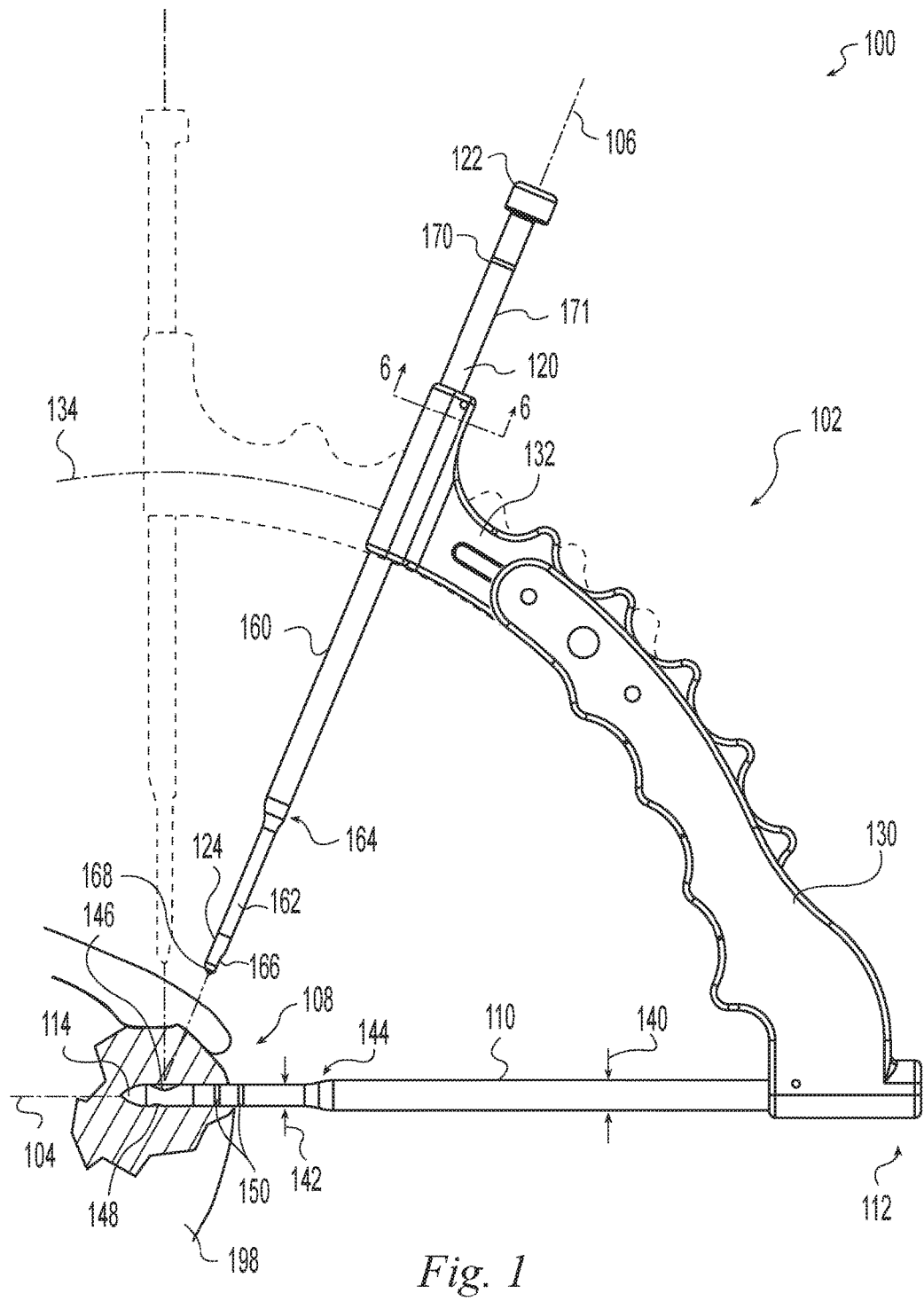
FIG. 1 is a side elevation view of an example of the invention illustrating an instrument engaged with a bone, the bone being shown in partial section.

The following illustrative examples depict instruments and methods to form a tunnel through a bone and pass a member through the bone tunnel. The illustrative examples depict passing a round suture through a bone tunnel to attach a soft tissue to the bone. However, the instruments and methods of the invention may be used to pass other elements through a bone tunnel including, suture passers, suture tapes, cables, soft tissues, grafts, and other elements. Examples of instruments and methods of the invention may be used to pass any member through any bone, at surgical sites anywhere in a patient's body, and for any purpose. The terms "suture" and "suture strand" are used herein to mean any strand or flexible member, natural or synthetic, able to be passed through a bone tunnel and useful in a surgical procedure. The term "transverse" is used herein to mean to cross at an angle; i.e. not parallel. The term includes, but is not limited to right angles.

FIGS. 1-8 depict examples of a guide and a passer for forming intersecting bone tunnels in a bone 198 and passing a flexible element through the tunnels. The exemplary guide 100 includes a guide body 102 defining a first insertion or guide axis 104 and a second insertion or guide axis 106 intersecting at a location 108 spaced from the guide body.

A first tunnel member 110 is engageable with the guide body 102 coaxial with the first guide axis 104 and includes a proximal end 112, a distal end 114, and a first longitudinal passage 116 (FIG. 7) at least partway through the first tunnel member 110.

A second tunnel member 120 is engageable with the guide body 102 coaxial with the second guide axis 106 and includes a proximal end 122, a distal end 124, and a second longitudinal passage 126 (FIG. 7) at least partway through the second tunnel member 120.

A passer 136 (FIG. 2) is operable to extend from the proximal end 122 of the second tunnel member 120, through the distal end 124 of the second tunnel member 120, through the distal end 114 of the first tunnel member 110, and to the proximal end 112 of the first tunnel member 110 in one continuous path. The passer 136 may then be used to pull a flexible element such as, for example, a passing suture or a repair suture through the tunnel members 110, 120 to pass the flexible element through, for example, a bone.

In the illustrative embodiment of FIGS. 1-8, the guide body 102 is made up of first and second arc members 130, 132. The first and second arc members 130, 132 are joined in sliding relationship along an arc shaped path 134 of constant radius such that the guide 100 is adjustable between a first position (shown in solid lines in FIG. 1) in which the first guide axis and the second guide axis define a first angle between them and a second position (shown in dashed lines in FIG. 1) in which the first guide axis and the second guide axis define a second, larger angle between them. Preferably, the guide is continuously adjustable over a range of included angles between the first and second guide axes 104, 106 of from 20 to 110 degrees. More preferably, the range is 60 to 90 degrees. In the illustrative example of FIGS. 1-8, the first guide axis 104 is defined by a passage in the first arc member 130 and the second guide axis 106 is defined by a passage in the second arc member 132.

The first tunnel member may include a drill guide, a punch guide, a punch, or other suitable member for forming a bone tunnel and/or for inserting into a bone tunnel. In the illustrative example of FIGS. 1-8, the first tunnel member 110 is a bone punch fixed to the guide body such as by pinning, threading, welding, or other suitable fixation method. For example, the first tunnel member 110 may be impacted into the bone 198 to form a bone tunnel in the bone. In the illustrative example of FIGS. 1-8, the first tunnel member 110 includes a cylindrical body having a first, larger diameter 140 near its proximal end 112 and a second, smaller diameter 142 near its distal end with a tapered transition region 144 between the two diameters. The cylindrical body defines a first outer side wall and a first recess or side opening 146 (FIG. 7) in the first side wall nearer the distal end 114 than the proximal end 112. The second guide axis 106 passes through the first side opening 146 for every angle in the range of adjustment of the first and second arc members 130, 132. The first longitudinal passage 116 extends from the proximal end 112 of the first tunnel member 110 toward the distal end 114 and communicates with the first side opening 146. A relief opening 148 in the side wall is positioned opposite the first side opening 146 and communicates with the first longitudinal passage 116 and the first side opening 146. The first tunnel member 110 includes indicia 150 (FIG. 1) on the outer surface readable relative to the bone surface to indicate a depth of penetration of the first tunnel member 110 into the bone. In the illustrative example of FIGS. 1-8, the indicia 150 include two separate marks to indicate the appropriate depth for two different sizes of anchor. In the illustrative example of FIGS. 1-8, the first tunnel member 110 tapers to a solid, sharp point 152 distal to the first side opening 146 and the relief opening to facilitate driving the first tunnel member 110 into bone.

The second tunnel member may include a drill guide, a punch guide, a punch, or other suitable member for forming a bone tunnel and/or inserting into a bone tunnel. In the illustrative example of FIGS. 1-8, the second tunnel member 120 is a punch engageable with the guide 100 in axial sliding relationship along the second guide axis 106. For example, the second tunnel member 120 may be impacted into the bone 198 to form a bone tunnel in the bone. In the illustrative example of FIGS. 1-8, the second tunnel member 120 includes a body having a "D"-shaped proximal portion 160 and a smaller cylindrical distal portion 162 with a tapered transition region 164 between the two portions. The body defines a second outer side wall and a second side opening 166 (FIG. 7) in the first side wall nearer the distal end 124 than the proximal end 122. In the illustrative example of FIGS. 1-8, the second longitudinal passage 126 extends from the proximal end 122 of the second tunnel member 120 toward the distal end 124 of the second tunnel member 120 and communicates with the second side opening 166. The second tunnel member 120 tapers to a solid, sharp point 168 distal to the second side opening 166 to facilitate driving the second tunnel member 120 into bone. The second tunnel member 120 includes an indicator to indicate when it is engaged with the first tunnel member 110. In one example, the second tunnel member 120 includes an index mark 170 on the outer surface readable relative to the guide 100 to indicate a depth of penetration of the second tunnel member 120 into the bone. In the illustrative example of FIGS. 1-8, the distal portion 162 of the second tunnel member 120 is engageable within the first side opening 146 of the first tunnel member with the first side opening 146 and second side opening 166 in communication with one another. The index mark 170 on the second tunnel member 120 indicates when the distal end of the second tunnel member 120 is seated in the first side opening 146. In another example, the second tunnel member 120 has an elongated marker such as for example a contrasting surface 171 that is exposed to indicate when the second tunnel member is not properly seated. The surface 171 extends proximally-distally the distance of the engagement of the second tunnel member 120 with the guide body 102. When the second tunnel member 120 is properly seated, the surface 171 is covered by the guide body 102. If the second tunnel member 120 is not fully seated, the surface 171 is visible above the guide body. If the second tunnel member is inserted to far, for example if is deflects upon insertion such that it misses the first tunnel member and is driven past the first tunnel member, the surface 171 is visible below the guide body. In one example, the surface 171 includes a colored stripe, for example a red colored stripe, such that if red is visible after inserting the second tunnel member it indicates that the second tunnel member is not properly seated. For example, in FIGS. 1 and 21 the surface 171 is visible above the guide body 102 and in FIGS. 5 and 22 the surface 171 is concealed by the guide body 100.

The relief opening 148 in the first tunnel member allows bone chips or other debris to exit the first tunnel member 110 when the second tunnel member 120 engages it. In the illustrative example of FIGS. 1-8, an angled surface 172 is formed at the distal end of the second longitudinal passage 126 facing the second side opening 166. The angled surface 172 deflects the passer 136 through the second side opening 166 and into the first longitudinal passage 116 when the passer is inserted. The "D"-shape of the proximal portion 160 of the second tunnel member 120 engages the guide 100 to prevent rotation of the second tunnel member 120 as it axially translates so that the first and second side openings 146, 166 are aligned when the first and second tunnel members 110, 120 are engaged.

The length of the first and second tunnel members 110, 120 that extends from the guide body to their intersection location may be any desired length. However, it has been found by the inventors that for rotator cuff repair surgery on a human shoulder, a length of each member in the range of 2-8 inches is useful. More preferably the length is in the range of 4-6 inches. The length for each member may be the same or different. In the example of FIGS. 1-8, the length of the first tunnel member extending from the guide body is approximately 5.5 inches and the length of the second tunnel member extending from the guide body is approximately 4.5 inches.

Figures 5, 6:
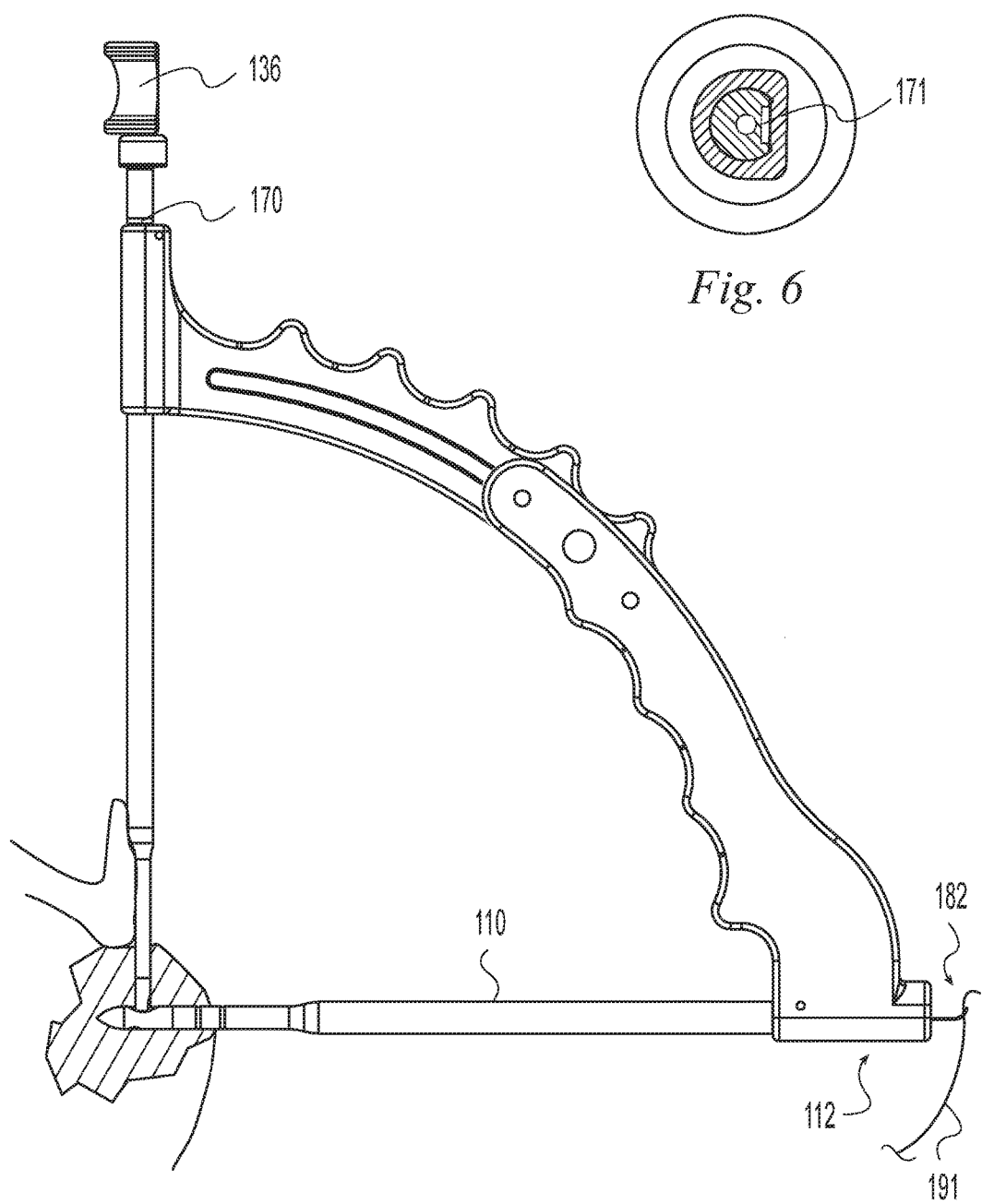
FIG. 5 is a side elevation view of the instrument of FIG. 1 engaged with a bone and the passer of FIG. 2 inserted through the instrument.
FIG. 6 section view taken along line 6-6 of FIG. 1.
Figure 7:
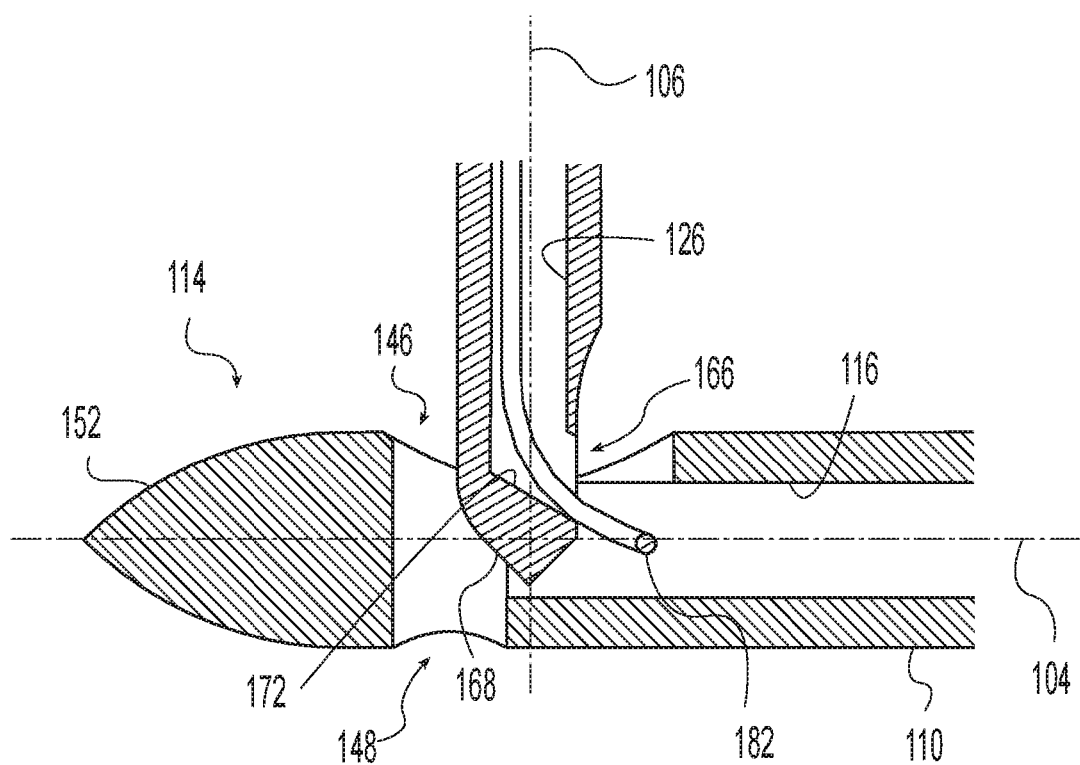
FIG. 7 is detail side section view of the instrument of FIG. 1 showing the passer engaged with the instrument in a first position.
Figure 8:
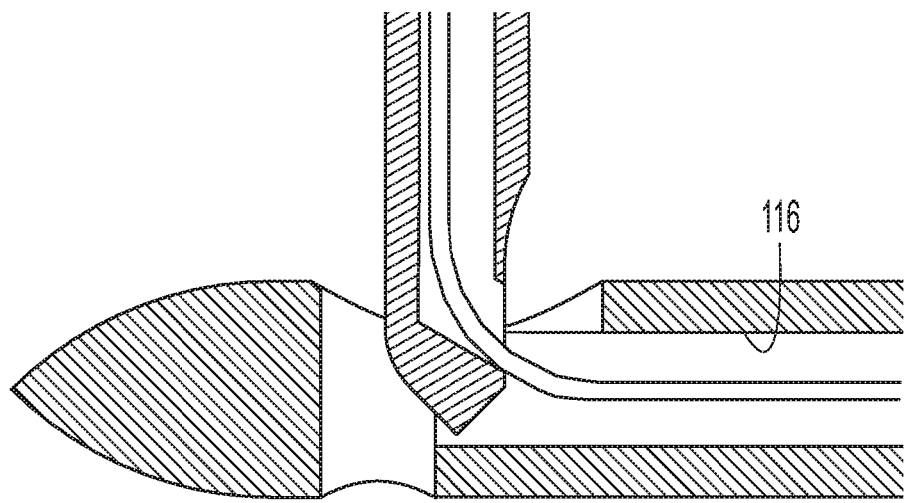
FIG. 8 is detail side section view of the instrument of FIG. 1 showing the passer engaged with the instrument in a second position.

The passer 136 includes a first, or proximal, end 180 and a second, or distal, end 182 defining a loop 188. In the illustrative example of FIGS. 1-8, the passer 136 includes a relatively rigid shaft 184 extending away from the first end and a relatively flexible wire 186 attached to the shaft 184 and extending away from the shaft 186. In one example, the shaft 184 is a tubular member and the wire 186 is crimped, bonded, soldered, welded or otherwise attached to the shaft. In the illustrative example of FIGS. 1-8, the wire 186 is formed into a loop 188 in a first plane and bent to form a curved profile 190 in a second plane perpendicular to the first plane. The curved profile 190 of the wire and the angled surface 172 at the distal end of the second longitudinal passage 126 cooperate to facilitate advancing the distal end 182 of the passer from the second longitudinal passage 126 into the first longitudinal passage 116. The passer 136 includes a handle 192 at the proximal end 180. Preferably, the passer, or at least the wire 186, is formed of a super elastic material. Preferably the combined length of the shaft 184 and wire 186 is greater than the combined length of the first and second longitudinal passages 116, 126 such that the passer 136 is insertable through the first and second tunnel members 110, 120 to extend through the first and second axial passages and out of the proximal end 112 of the first tunnel member 110 and out of the proximal end 122 of the second tunnel member 120. For example, as the distal end 182 of the passer reaches the distal end of the second longitudinal passage 126, it abuts the angled surface 172 and is deflected out through the second side opening 166, through the first side opening 146 and into the first longitudinal passage 116 (FIG. 7). The curved profile 190 of the wire and angled surface 172 facilitate the transition of the wire 186 from the second tunnel member 120 to the first tunnel member 110 and promote passage even when the first and second tunnel members 110, 120 are engaged at an acute angle. The passer is further advanced to move the distal end 182 of the passer through the second longitudinal passage and out the proximal end 112 of the first tunnel member 110 (FIG. 5). A member 191, e.g. a suture, may be placed in the loop 188 at the distal end 182 of the passer and the passer 136 may be retrieved to pull the member 191 through the first longitudinal passage 116, through the first side opening 146, through the second side opening 166, through the second longitudinal passage 126 and out the proximal end of the second longitudinal passage 126. The passer handle includes an indicator, for example a flat surface 197, to indicate to a user the orientation of the bent loop so that the user can orient it to engage the angled surface 172. Alternatively, or in addition, the passer may be keyed to the second tunnel member to permit only one orientation.

Figure 9:
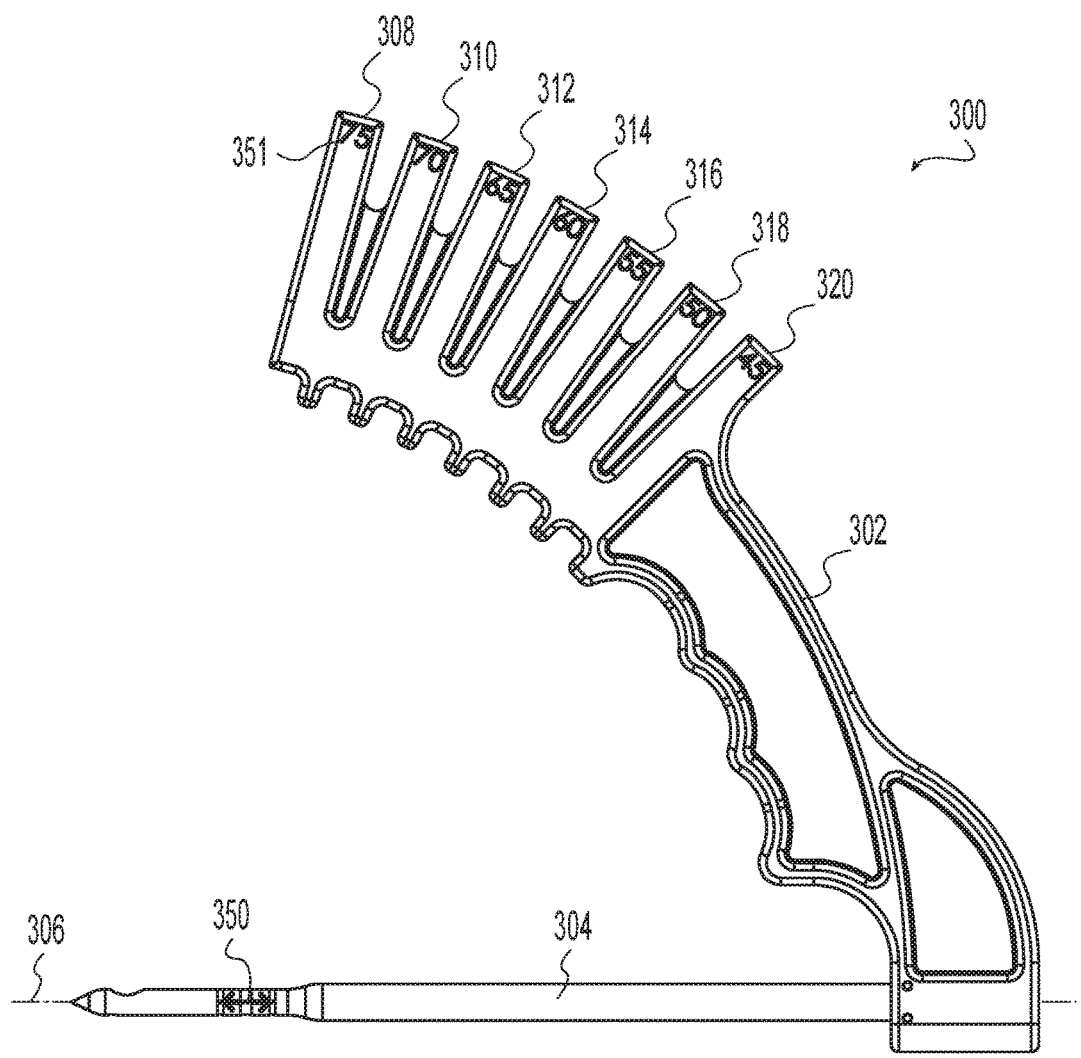
FIG. 9 is a side elevation view of an example of the invention illustrating an alternative arrangement of the instrument of FIG. 1.
Figure 10:
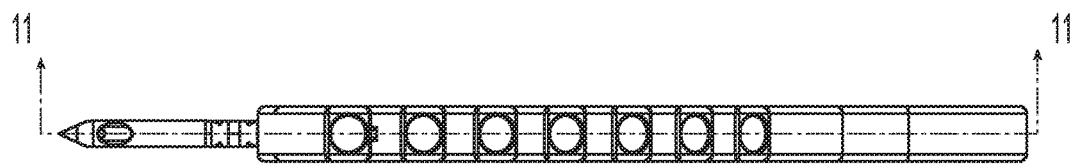
FIG. 10 is a top plan view of the instrument of FIG. 9.
Figure 11:
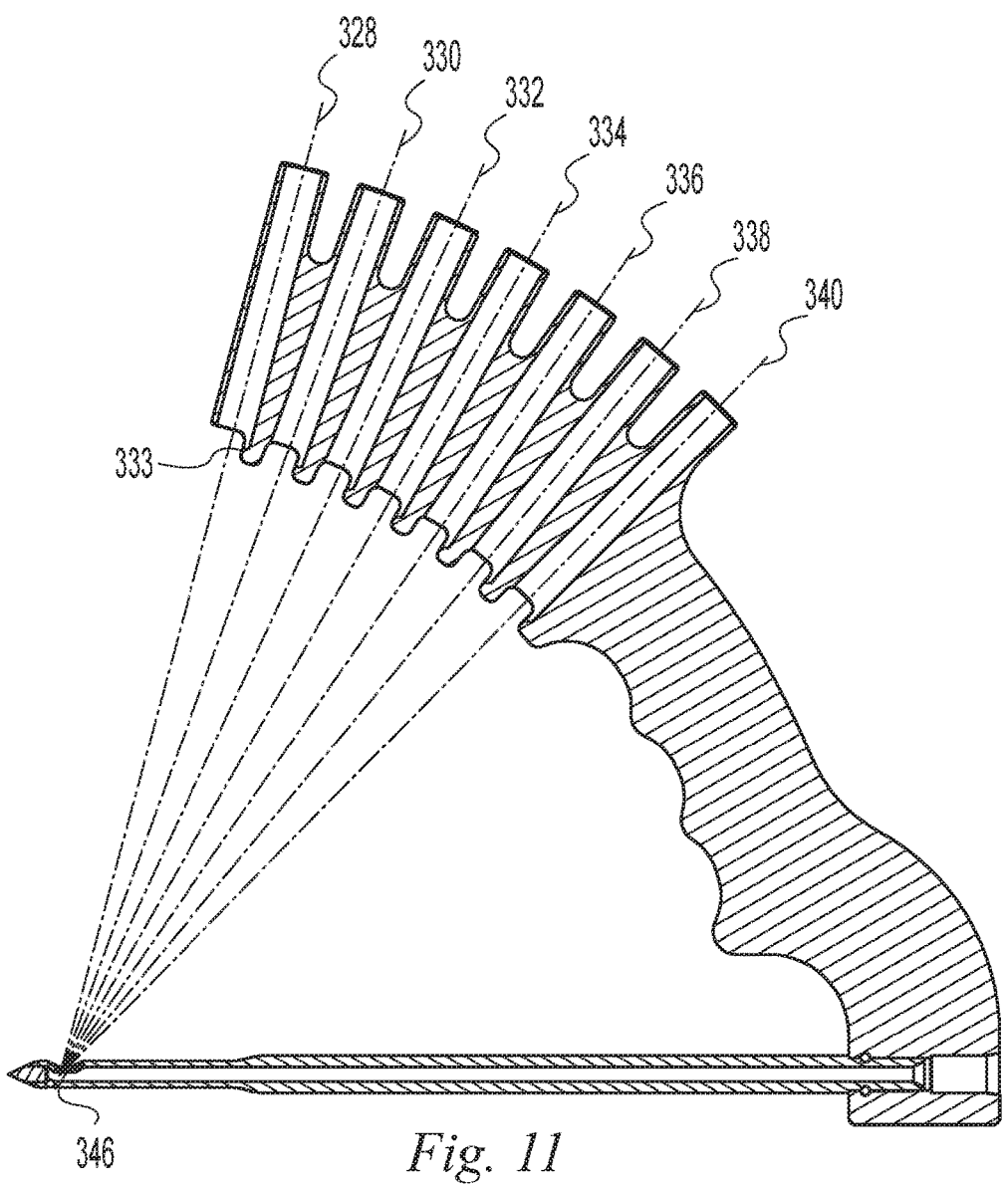
FIG. 11 is a section view taken along line 11-11 of FIG. 10.

FIGS. 9-11 illustrate another example of a guide instrument 300 similar to that of FIG. 1 but showing a different arrangement of the second guide axis. The guide body 302 includes a first tunnel member 304 like the first tunnel member in the example of FIG. 1 that defines a first guide axis 306 as with the example of FIG. 1. However, the guide body is a unitary body having a plurality of receivers 308, 310, 312, 314, 316, 318, 320 operable to receive the second tunnel member 120. Each receiver includes a passage defining a guide axis. Any number of receivers may be included at any desired spacing to provide a desired selection of guide angles relative to the first guide axis. In the example of FIGS. 9-11, seven receivers are provided defining a second guide axis 328, a third guide axis 330, a fourth guide axis 332, a fifth guide axis 334, a sixth guide axis 336, a seventh guide axis 338, and an eighth guide axis 340. Each of the second through eighth guide axes intersects the first guide axis 304 at the same location spaced from the guide body and each can selectively receive the second tunnel member. In the example of FIGS. 9-11, each of the second through eighth guide axes intersects a side opening 346 in the first tunnel member like the side opening 146 in the example of FIG. 1. A surface 333 formed at the distal end of each receiver engages the flat side of the "D"-shaped second tunnel member 120 to prevent rotation of the second tunnel member 120 within the receiver so that the first and second side openings 146, 346 are properly aligned when the first and second tunnel members are engaged.

In the example of FIGS. 9-11, the second through eighth guide axes are equally spaced and define angles of 45 degrees to 75 degrees relative to the first guide axis 306. Indicia 350 on the first tunnel member 304 indicates an insertion depth range suitable for a fastener, for example a knotless fastener. Indicia 351 on each receiver indicates the angle corresponding to each receiver. The spacing can be any desired spacing and can be uniform or non-uniform to provide a range of angles useful to the user. The inventors have found the spacing and range shown in the example to be suitable for typical rotator cuff procedures of the human shoulder.

For other applications such as for example for attaching soft tissue to a bone adjacent a knee joint, ankle or other location different spacing and angular range may be desirable. Similarly, the length of the first and second tunnel member may be varied. For example, for repairing a torn Achilles tendon, a guide having an angular range of 50 to 80 degrees has been found suitable with either a sliding adjustable guide like that of FIG. 1 or a unibody guide like that of FIG. 9. In a unibody guide, four receivers defining axes at 50, 60, 70 and 80 degrees relative to the first guide axis have been found to be suitable. Any length of first and second tunnel members may be used. However, for repairing a torn Achilles tendon, shorter lengths may advantageously be used. For example, first and second tunnel members each extending from the guide body a distance in the range of two to three inches has been found suitable.

Figure 12:
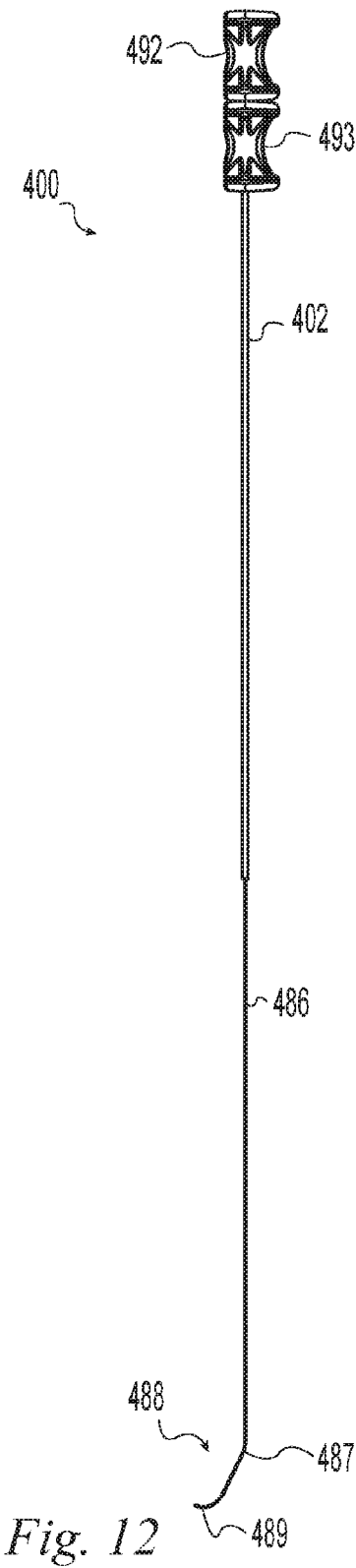
FIG. 12 is a side elevation view of an example of the invention illustrating an alternative arrangement of the passer of FIG. 2 in a first position.
Figure 13:
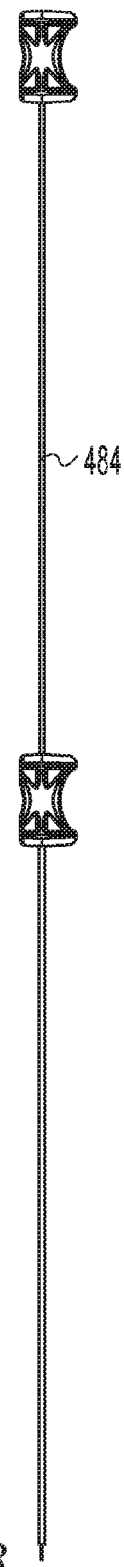
FIG. 13 is a side elevation view of the example of FIG. 12 in a second position.

FIGS. 12-13 illustrate another arrangement for a passer 400 similar to that of FIG. 2. The passer 400 includes an outer tube 402 engaged coaxially with the shaft 484 in axial sliding relationship and moveable relative to the shaft from a first position in which the outer tube encloses a portion of the wire length (FIG. 13) and a second position in which the outer tube encloses less of the wire length (FIG. 12). The outer tube is relatively rigid relative to the wire 486. The outer tube aids in inserting the passer 400 into the second tunnel member by holding the wire 486 in a straight and rigid configuration when the tube is in the first position. The outer tube may enclose any portion of the wire length in the first position to aid in inserting the passer. Preferably, in the first position, the outer tube encloses more than one-half of the wire length; more preferably 60 to 100 percent of the wire length; more preferably 80 to 100 percent of the wire length; more preferably the entire wire length including all of the loop 488. In the second position, enough of the wire is exposed to allow it to extend through the side openings in the first and second tunnel members and through the first tunnel member. Preferably in the second position, the outer tube encloses less than one-half of the wire length; more preferably less than 20 percent of the wire length. The tube may be inserted into the second tunnel member while in the first position and then shaft 484 advanced to extend the wire 486 out of the outer tube and through the second and first tunnel members. For example, a handle 492 on the shaft may be pressed toward a handle 493 on the outer tube to advance the wire. The loop 488 in the example of FIGS. 12 and 13 includes a first bend 487 angled away from the main portion of the wire 486 and a second bend 489 at the distal end forming a small radius. The bends 487, 489 facilitate the transition of the loop through the side openings of the tunnel members.

Figure 14:
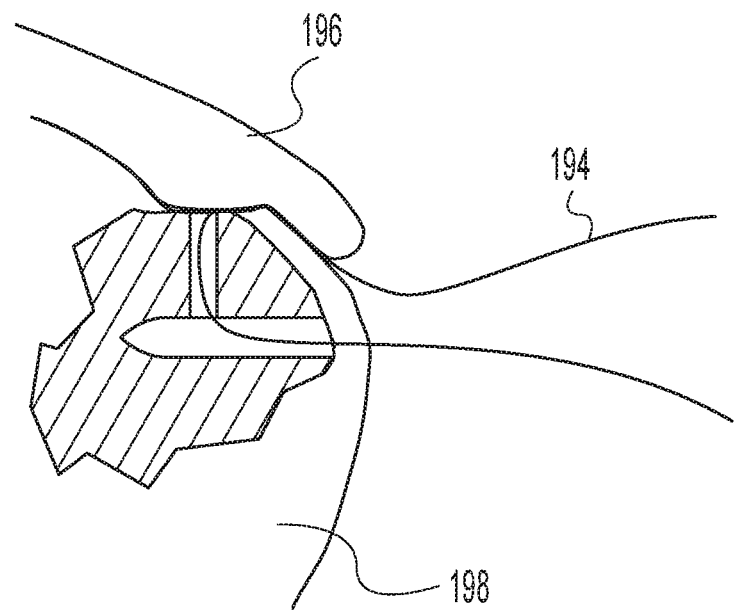
FIG. 14 is a partial sectional view of the bone of FIG. 1 after a suture has been passed and the passing instruments have been removed.
Figure 15:
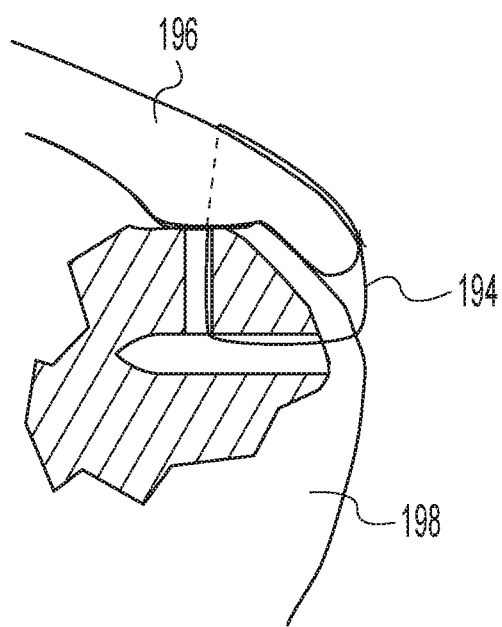
FIG. 15 is a partial sectional view illustrating the suture of FIG. 14 in use to secure a soft tissue to the bone.

The exemplary guides and methods of the invention make it possible to form intersecting bone tunnels in a bone and extend, in one motion, a passer through the guide and bone tunnels from a first position external to the bone to a second position external to the bone. A first end of a member, such as a suture, may then be engaged with the passer outside of the bone tunnels. By having the engaging step outside of the bone tunnels, it may be done with simple manual manipulation of the passer loop and the first end of the member with easy access and visibility and without specialized arthroscopic instrument or procedures. The first end of the member may then be passed, in one motion, through the guide and bone tunnels from the second position external to the bone to a first position external to the bone to thread the member through the intersecting bone tunnels. The member may be used in any desirable manner. For example, a member in the form of a suture 194 may be so passed and then used to secure soft tissue 196 to the bone 198 as shown in FIGS. 14 and 15.

Figure 16:
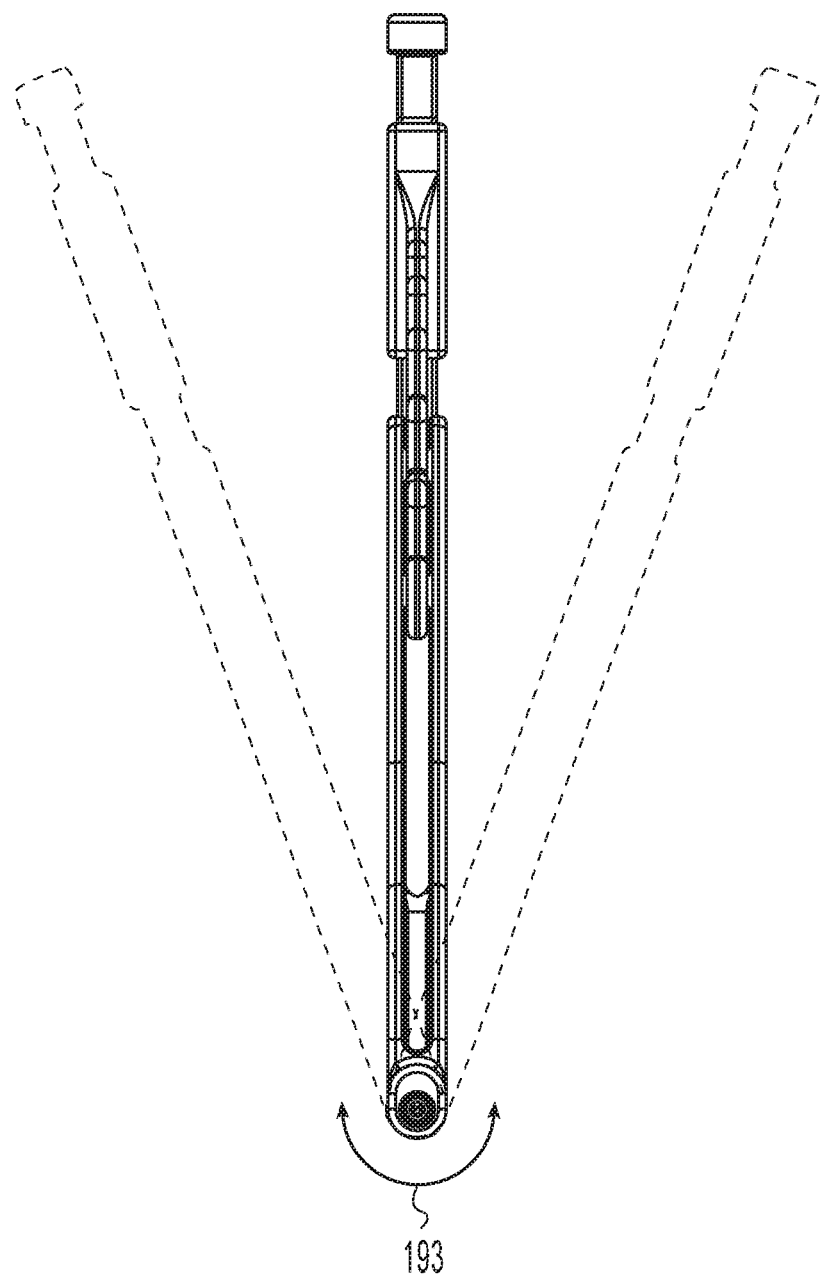
FIG. 16 is a rear elevation view of the guide of FIG. 1 illustrating how it can be rotated while engaged with a bone.
Figure 17:
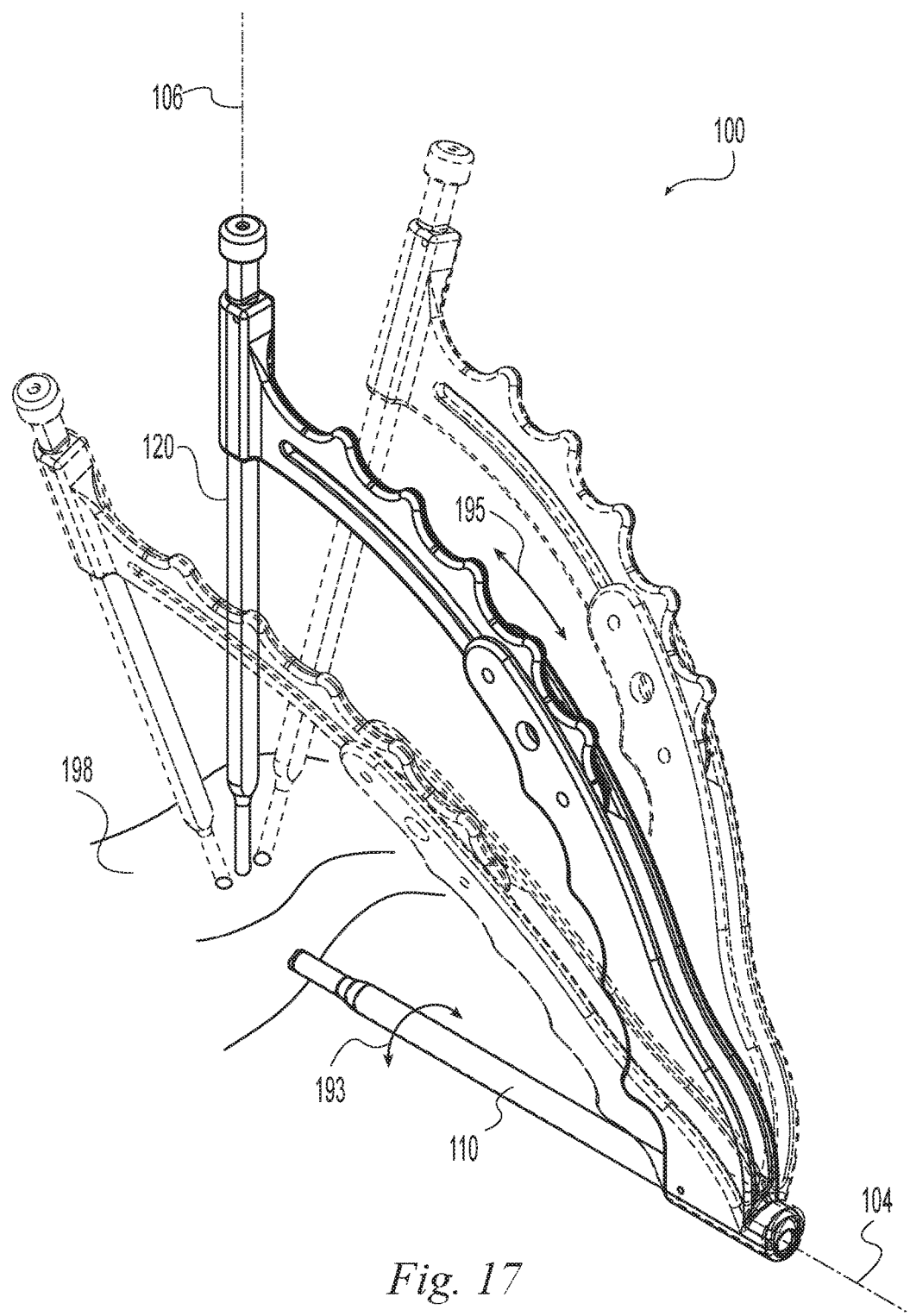
FIG. 17 is a perspective view of the guide of FIG. 1 illustrating how it can be rotated while engaged with a bone.

Referring to FIGS. 16 and 17, a guide according to examples of the invention, for example guide 100 as shown in FIGS. 16 and 17, may be used to create three or more intersecting tunnels and pass flexible elements through the tunnels. For example, after passing a first flexible element through first and second intersecting tunnels in a bone 198, the second tunnel member 120 may be withdrawn from the bone. The guide 100 may be rotated about the first guide axis 104, as shown at reference numeral 193, and/or the angle between the guide axes 104 may be adjusted as shown at reference numeral 195 in FIG. 17. In a unitary guide such as the example of FIG. 9, the angle between the guide axes may be adjusted by inserting the second tunnel member in a different receiver. The second tunnel member 120 may then be inserted into the bone 198 in a new location and advanced to form a third bone tunnel intersecting the first bone tunnel. The second tunnel member 120 may be engaged with the first tunnel member 110 and the passer 136 used to pass a second flexible element through the first and third tunnels. This may be repeated as many times as desired to provide a one-to-many relationship between the first bone tunnel and the plurality of additional bone tunnels intersecting the first bone tunnel. The third and subsequent bone tunnels may be formed and the second and subsequent flexible elements may be passed while the first tunnel member 110 remains in the bone and while the first flexible element remains in the first tunnel member.

FIGS. 18-27 illustrate an example of a surgical method according to the invention. In the illustrative example of FIGS. 18-27, instruments and methods of the previous examples are shown in use to place transosseous sutures to repair a rotator cuff 202 of a shoulder joint. It will be understood that any of the examples of instruments and methods of the invention may be used in any combination to pass a member through a shoulder bone or other bones at a shoulder or other surgical sites and for rotator cuff repair or other surgical purposes.

Figure 18:
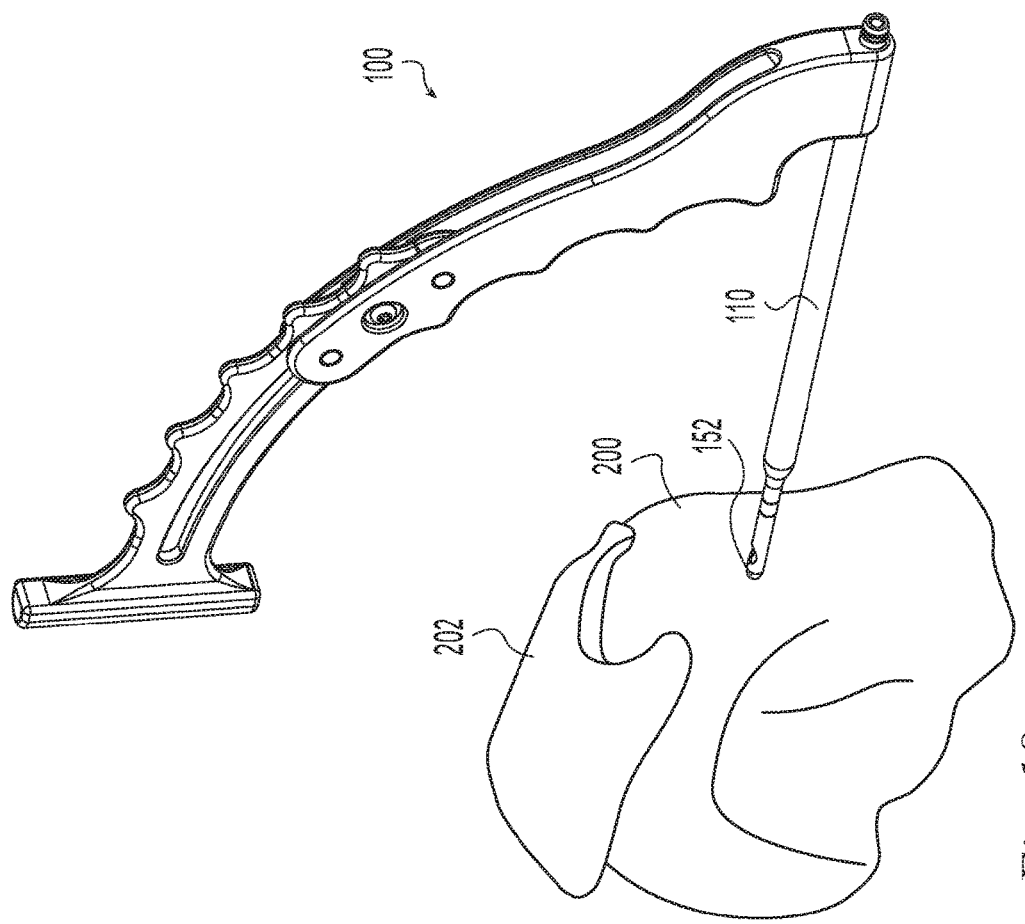
FIGS. 18-28 are perspective views of methods according to examples of the invention.

Referring to FIG. 18 the guide 100 is positioned with the point 152 of the first tunnel member 110 on the lateral surface of the greater tuberosity 200 of the humerus approximately 30 mm inferior to the superior border of the tuberosity. The guide 100 is oriented such that it is perpendicular to the long axis of the humerus and perpendicular to the acromion (not shown).

Figure 19:
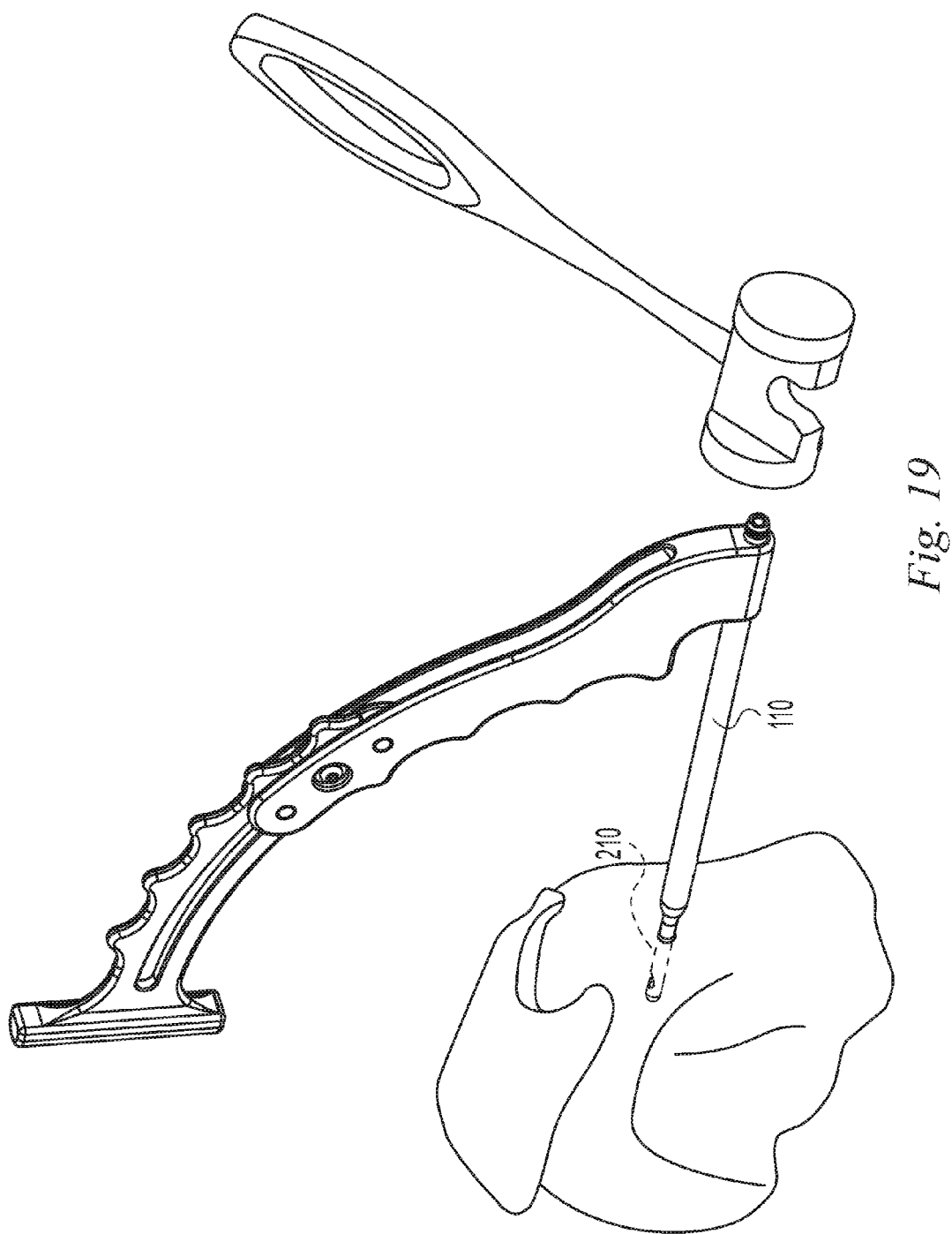

Referring to FIG. 19, the first tunnel member 110 is impacted into the bone to form a first, or lateral, bone tunnel 210.

Figure 20:
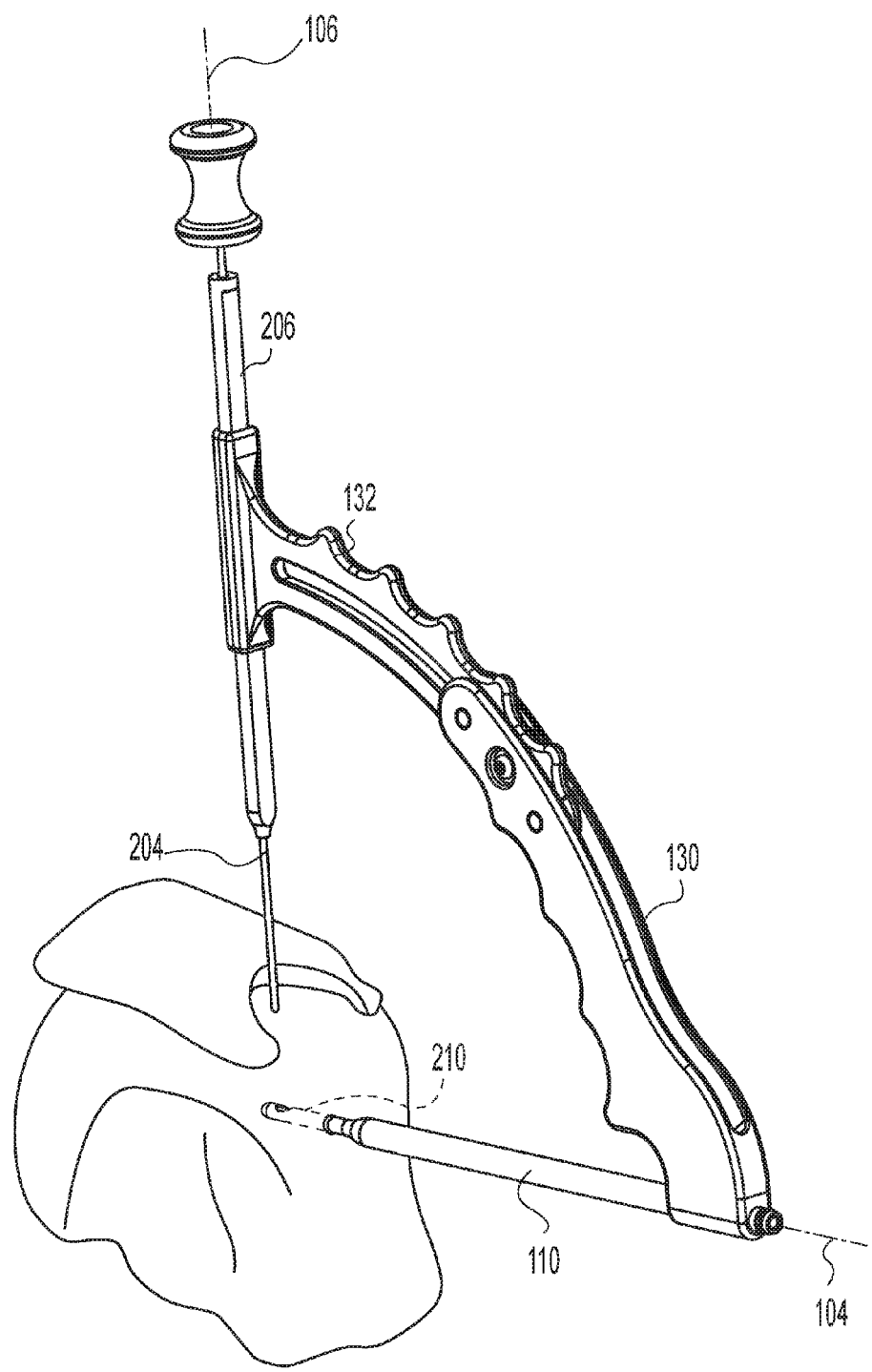

Referring to FIG. 20, the location for a second, or medial, tunnel is visualized using a targeting wire 204 in a targeting sleeve 206 to constrain the wire 204 to translation along the second guide axis 106. The position of the targeting wire may be adjusted in two degrees of freedom. First, the guide 100 may be rotated about the first guide axis 104 by twisting the first tunnel member 110 in the lateral bone tunnel 210. Second, the guide may be repositioned by adjusting the first and second arc members 130, 132 to change the angle between the guide axes 104, 106 (or repositioning the targeting sleeve and targeting wire in a different receiver in a unitary guide such as that of FIG. 9). As these adjustments are made, the targeting wire 204 may be inserted through the skin and other soft tissues near the targeted site so that the position may be visualized on the bone. The small punctures in the skin and other soft tissues created by the targeting wire 204 cause minimal trauma to the tissues and facilitate multiple targeting attempts if needed. The targeting wire 204 is then used to mark the bone surface with the desired medial tunnel location.

Figure 21:
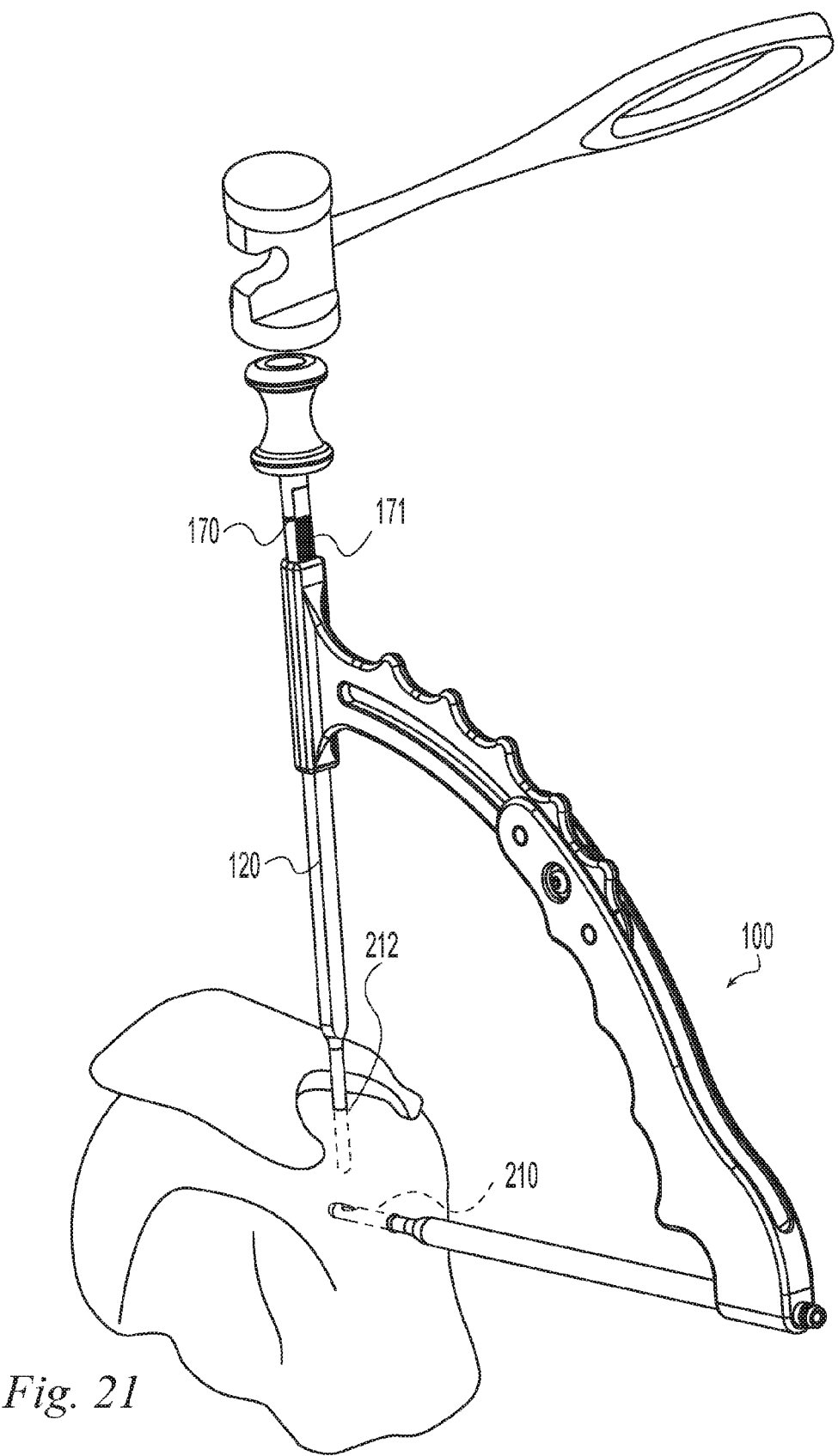

Referring to FIG. 21, the targeting sleeve and wire are removed and the second tunnel member 120 is impacted to form a second, or medial, tunnel 212.

Figure 22:
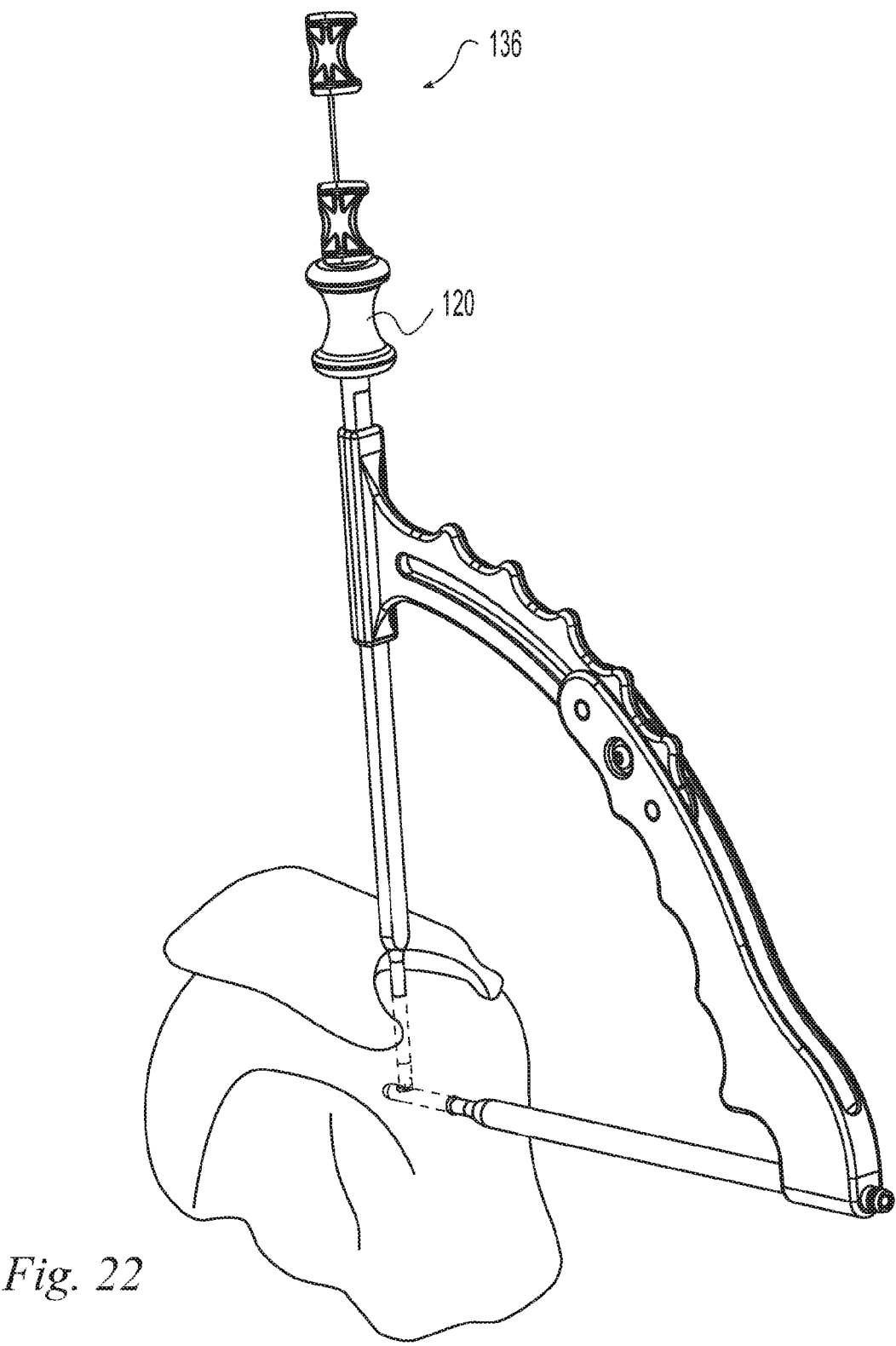

Referring to FIG. 22, the second tunnel member 120 is engaged with the first tunnel member 110 and the passer 400 inserted into the second tunnel member 120.

Figure 23:
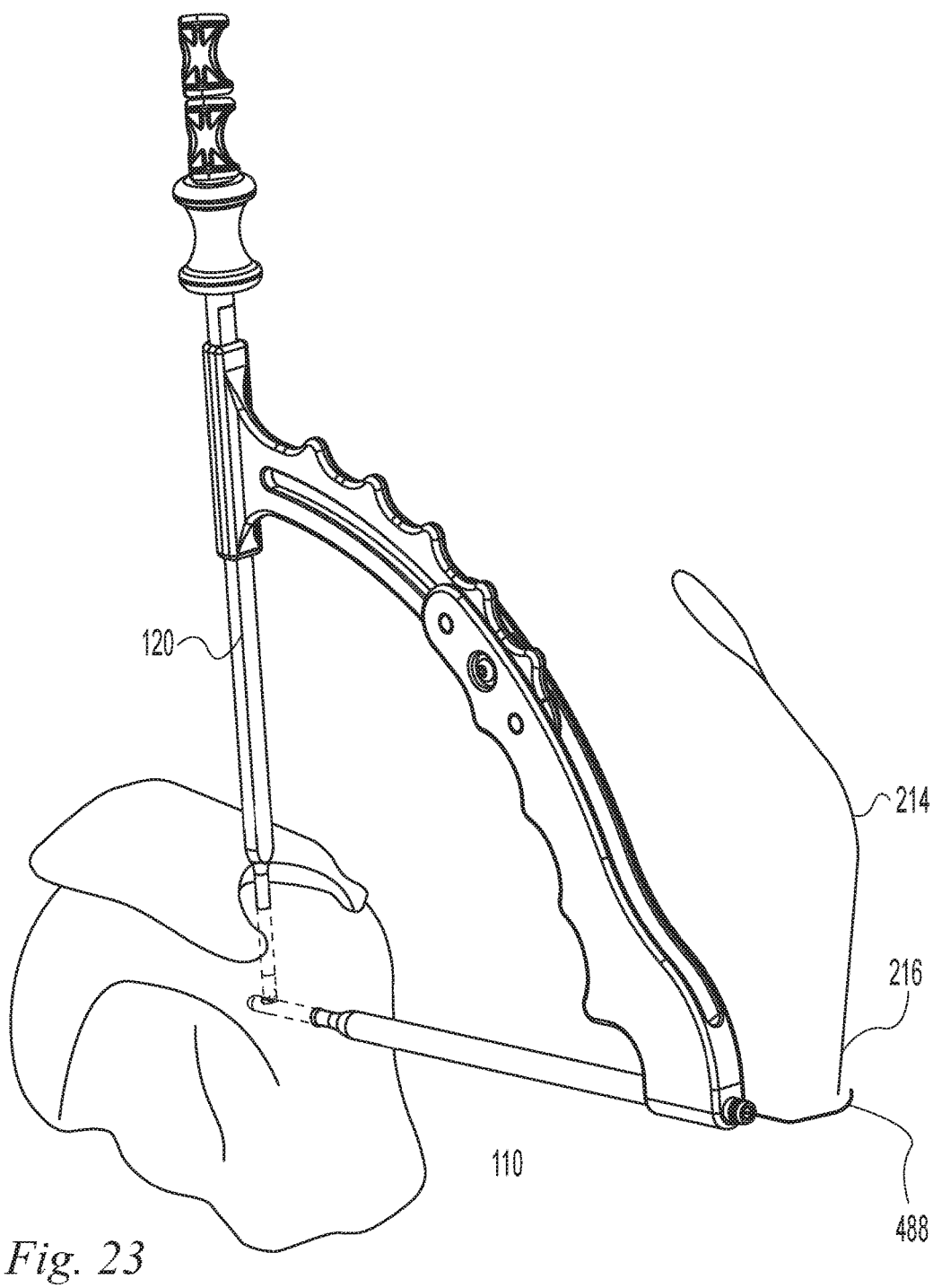

Referring to FIG. 23, the wire is advanced through the first and second tunnel members 110, 120 until it extends from the proximal end of the first tunnel member 110. The end 216 of a first shuttle suture 214 is passed through the loop 488 of the passer 400.

Figure 24:
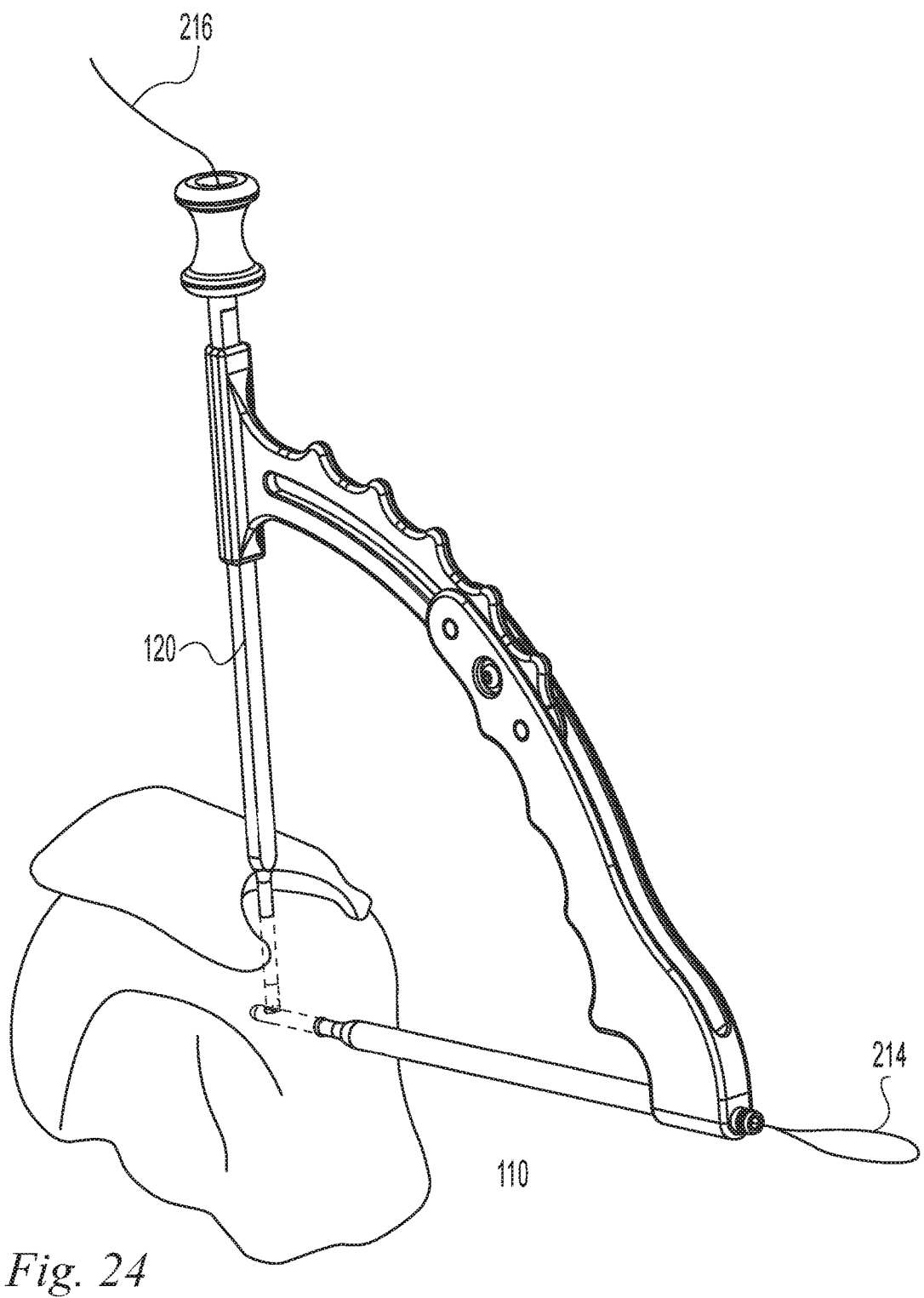

Referring to FIG. 24, the end 216 of the shuttle suture 214 is retrieved by pulling the passer 136 out the distal end of the second tunnel member 120.

Figure 25:
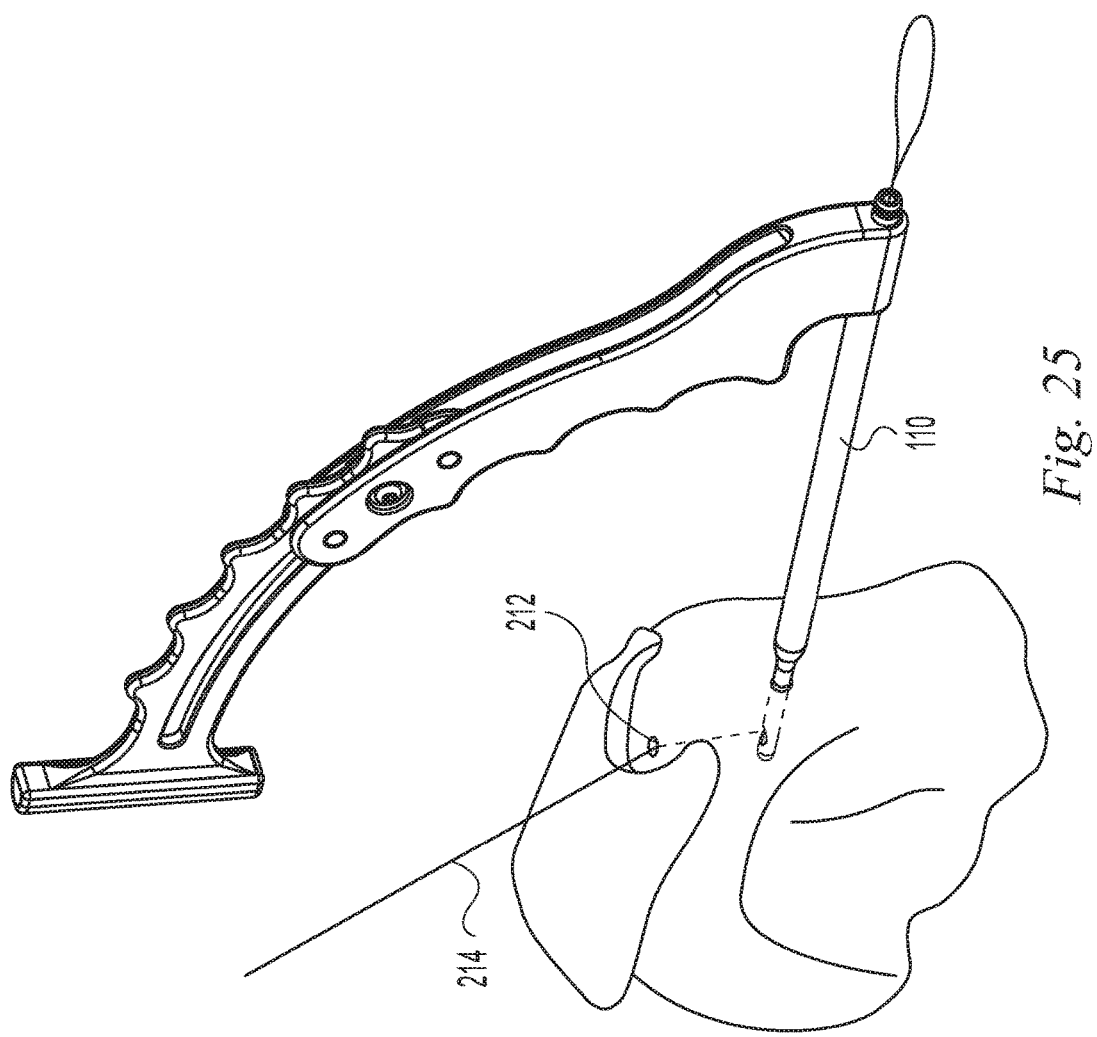

Referring to FIG. 25, the second tunnel member 120 is removed leaving the first shuttle suture 214 in place in the first tunnel member 110 and extending out of the second, medial bone tunnel 212.

Figure 26:
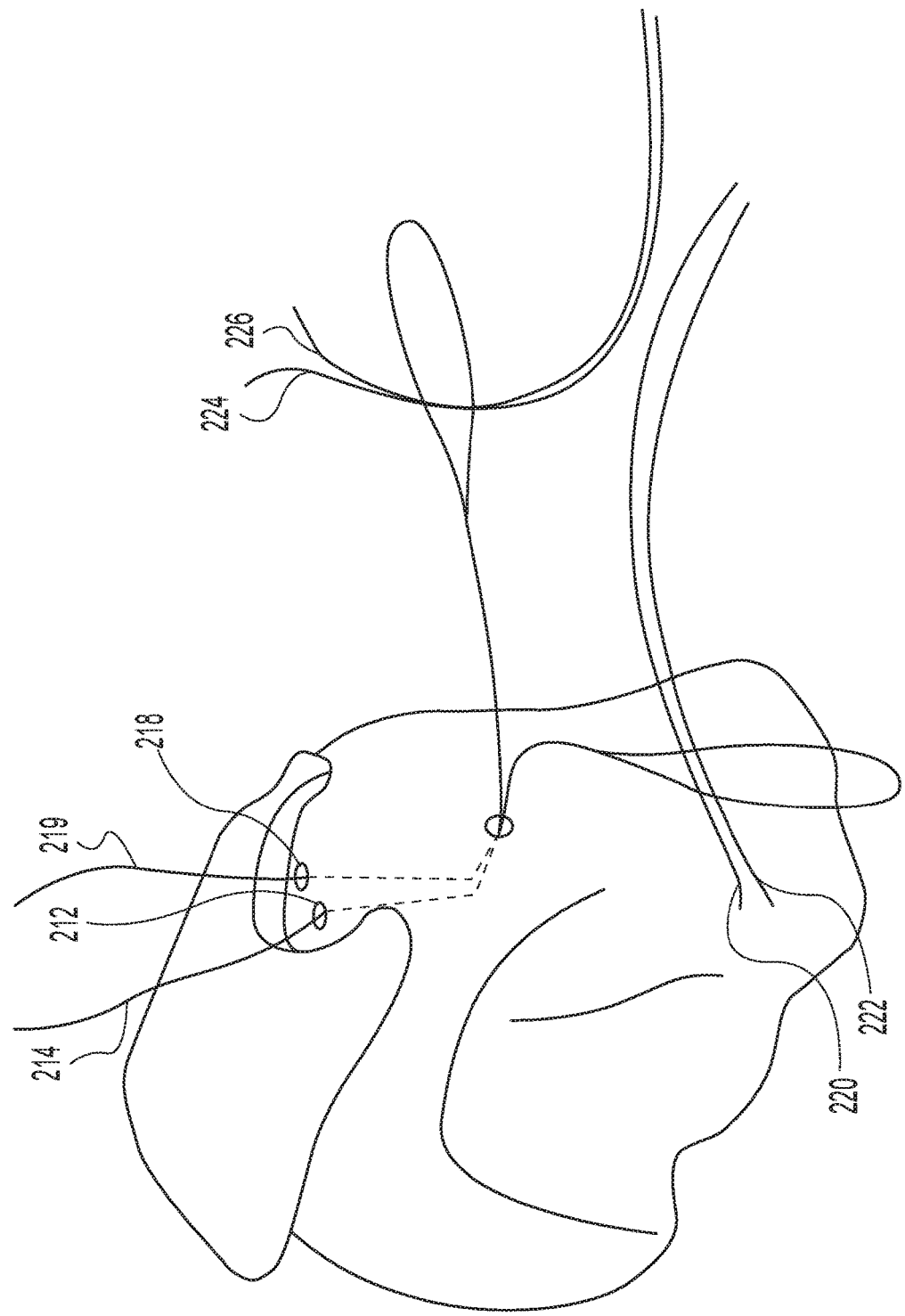
Figure 27:
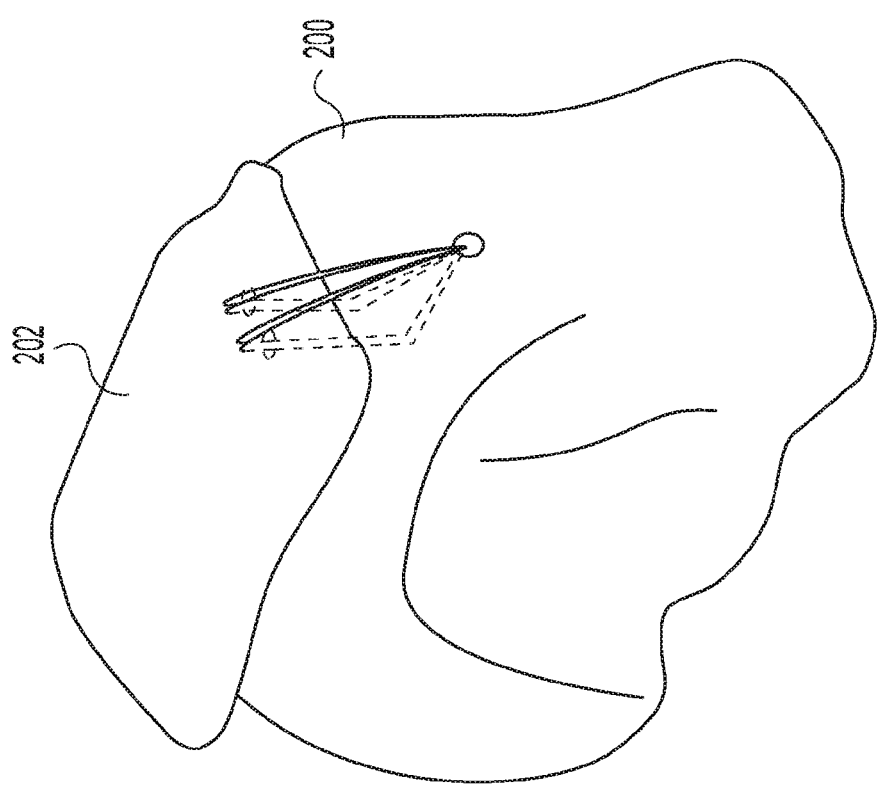

Referring to FIGS. 26 and 27, the preceding steps are repeated to create a third, additional medial, tunnel 218 and place a second shuttle suture 219 while the first tunnel member 110 remains in the bone and while the first shuttle suture 214 remains in the first tunnel member 110. Two limbs 220, 222 of a first repair suture are passed through the loop of the first shuttle suture 214 and two limbs 224, 226 of a second repair suture are passed through the loop of the second shuttle suture 219. The shuttle sutures 214, 219 are pulled to pass the limbs of the repair sutures through the bone. The repair sutures are passed through the rotator cuff 202 and used to secure it to the humerus 200.

Figure 28:
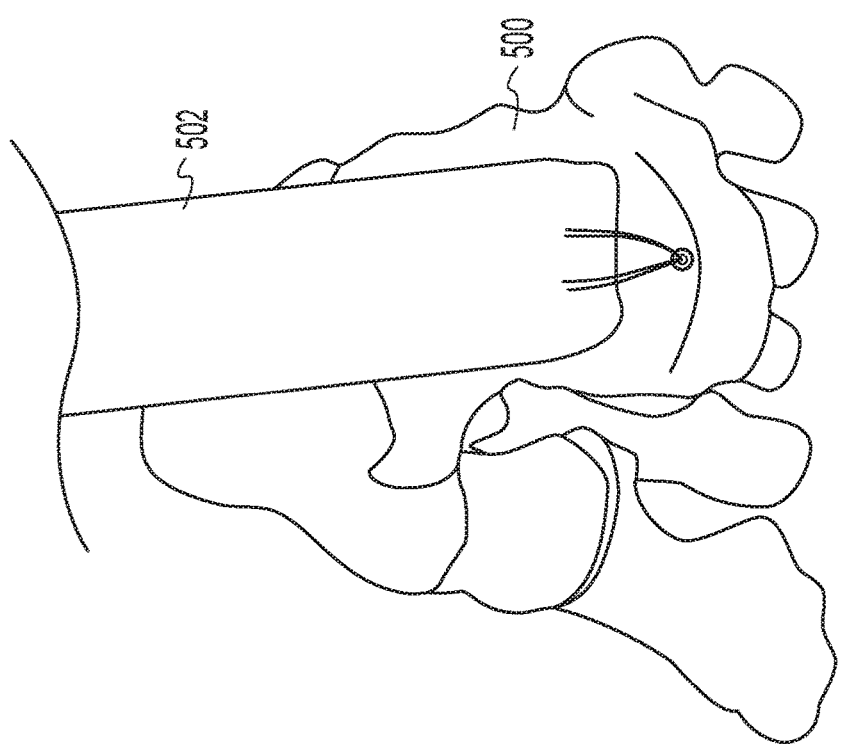

Referring to FIG. 28 the instruments and methods may also be used for other repairs such as, for example, an Achilles tendon repair in which the first and second tunnel members are inserted into the heel bone 500 and one or more sutures are passed and used to secure the Achilles tendon 502 to the bone 500.

While the illustrative examples have shown bone tunnels being formed by punching instruments into the bone, it is also within the scope of the invention to form bone tunnels by drilling, reaming, broaching, and/or any suitable tunnel forming process. It is contemplated, and within the scope of the invention, that the various features of the illustrative examples may be interchanged among the illustrative examples.

The following are further examples of the invention
1. An instrument for placing a member transosseously through first and second transverse, intersecting bone tunnels, the instrument comprising:
    a guide body defining a first guide axis and a second guide axis, the first guide axis and the second guide axis intersecting at a location spaced from the guide body;
    a first tunnel member engaged with the guide body coaxial with the first guide axis, the first tunnel member having a proximal end and a distal end, the first tunnel member having a first longitudinal passage at least partway through the first tunnel member;
    a second tunnel member engaged with the guide body coaxial with the second guide axis, the second tunnel member having a proximal end and a distal end, the second tunnel member having a second longitudinal passage at least partway through the second tunnel member; and
    a passer operable to extend from the proximal end of the second tunnel member, through the distal end of the second tunnel member, through the distal end of the first tunnel member, and to the proximal end of the first tunnel member in one continuous path.
2. The instrument of example 1 wherein the first and second guide axes define a guide angle between them, the guide angle being adjustable.
3. The instrument of example 1 wherein the guide body includes a first arc member and a second arc member, the first arc member and the second arc member being joined in sliding relationship along an arc shaped path of constant radius, the guide body being adjustable between a first position in which the first guide axis and the second guide axis define a first angle between them and a second position in which the first guide axis and the second guide axis define a second angle between them, the second angle being greater than the first angle.
4. The instrument of example 3 wherein the first guide axis is defined by a passage in the first arc member and the second guide axis is defined by a passage in the second arc member.
5. The instrument of example 3 wherein the first angle and the second angle are in the range of 20 to 110 degrees.
6. The instrument of example 5 wherein the first angle and the second angle are in the range of 60 to 90 degrees.
7. The instrument of example 1 further comprising third and fourth guide axes, the second, third, and fourth guide axes intersecting the first guide axis at the same location on the first guide axis.
8. The instrument of example 1 wherein the first tunnel member is fixed to the guide body.
9. The instrument of example 1 wherein the first tunnel member comprises a drill guide.
10. The instrument of example 1 wherein the first tunnel member comprises a bone punch.
11. The instrument of example 10 wherein the first tunnel member includes a first side wall and a first side opening in the first side wall nearer the distal end than the proximal end, the first longitudinal passage extending from the proximal end of the first tunnel member toward the distal end of the first tunnel member and communicating with the first side opening.
12. The instrument of example 11 wherein the second guide axis passes through the first side opening.
13. The instrument of example 11 wherein the first tunnel member includes a relief opening through the side wall opposite the first side opening and communicating with the first longitudinal passage and first side opening.
14. The instrument of example 11 wherein the first tunnel member includes indicia on an outer surface and operable to align with a bone surface to indicate a depth of penetration of the first tunnel member into a bone corresponding to a predetermined tunnel depth.
15. The instrument of example 1 wherein the second tunnel member is separate from the guide body and the second tunnel member engages the guide body in axial sliding relationship along the second guide axis.
16. The instrument of example 1 wherein the second tunnel member comprises a drill guide.
17. The instrument of example 1 wherein the second tunnel member comprises a bone punch.
18. The instrument of example 17 wherein the second tunnel member includes a second side wall and a second side opening in the second side wall nearer the distal end than the proximal end, the second longitudinal passage extending from the proximal end of the second tunnel member toward the distal end of the second tunnel member and communicating with the second side opening.
19. The instrument of example 18 wherein the first tunnel member includes a first side wall and a first side opening in the first side wall nearer the distal end than the proximal end, the first longitudinal passage extending from the proximal end of the first tunnel member toward the distal end of the first tunnel member and communicating with the first side opening, the first tunnel member and second tunnel member being engageable at their distal ends so that the first side opening and second side opening are in communication with one another.
20. The instrument of example 19 wherein the distal end of the second tunnel member is operable to insert into the first side opening with the second side opening in communication with the first side opening.
21. The instrument of example 20 further comprising an angled surface at the distal end of the second longitudinal passage, the angled surface facing the second side opening, the angled surface operable to deflect the passer through the second side opening.
22. The instrument of example 1 wherein the passer comprises a first end and a second end, the passer defining a loop at its second end.
23. The instrument of example 1 wherein the passer is formed of a super elastic material.
24. The instrument of example 1 wherein the passer has a length greater than the combined length of the first and second longitudinal passages.
25. The instrument of example 22 wherein the loop is bent.
26. The instrument of example 22 wherein the passer comprises a shaft and a wire extending from the shaft, the shaft extending away from the first end, the shaft having a shaft length, the shaft being relatively rigid compared to the wire, the wire being attached to an end of the shaft and extending away from the shaft to the second end where the wire defines the loop, the wire extending from the rigid shaft a wire length, the wire being relatively flexible compared to the shaft.
27. The instrument of example 26 wherein the passer further comprises an outer tube engaged with the shaft in axial sliding relationship and moveable relative to the shaft from a first position in which the outer tube encloses a portion of the wire length and a second position in which the outer tube encloses less of the wire length.
28. An instrument for placing a member transosseously through first and second transverse, intersecting bone tunnels in a bone, the instrument comprising:
a guide body defining a first guide axis and a second guide axis, the first guide axis and the second guide axis intersecting at a location spaced from the guide body;
a first tunnel member engageable with the guide body coaxial with the first guide axis, the first tunnel member having an outer surface, a proximal end, a distal end, and a first longitudinal passage at least partway through the first tunnel member, the first tunnel member outer surface having a recess formed therein and communicating with the first longitudinal passage;
a second tunnel member engaged with the guide body coaxial with the second guide axis, the second tunnel member having an outer surface, a proximal end, a distal end, and a second longitudinal passage at least partway through the second tunnel member, the second tunnel member outer surface having an opening formed therein and communicating with the second longitudinal passage, the recess of the first tunnel member being operable to receive the distal end of the second tunnel member with the opening communicating with the recess, wherein the first longitudinal passage, recess, opening, and second longitudinal passage form a continuous passage from the proximal end of the first tunnel member to the proximal end of the second tunnel member.
29. The instrument of example 28 wherein the recess is transverse to the first longitudinal axis and the opening is transverse to the second longitudinal axis.
30. The instrument of example 28 further comprising a passer having an elongate flexible portion operable to simultaneously extend through both the first and second longitudinal passages while the second tunnel member is received in the recess of the first tunnel.
31. The instrument of example 28 wherein the guide body includes a first arc member and a second arc member, the first arc member and the second arc member being joined in sliding relationship along an arc shaped path of constant radius, the guide body being adjustable between a first position in which the first guide axis and the second guide axis define a first angle between them and a second position in which the first guide axis and the second guide axis define a second angle between them, the second angle being greater than the first angle.
32. The instrument of example 31 wherein the first guide axis is defined by a passage in the first arc member and the second guide axis is defined by a passage in the second arc member.
33. The instrument of example 31 wherein the first angle and the second angle are in the range of 20 to 110 degrees.
34. The instrument of example 31 wherein the first angle and the second angle are in the range of 60 to 90 degrees.
35. The instrument of example 28 wherein the first tunnel member is fixed to the guide body.
36. The instrument of example 28 wherein the first tunnel member comprises a drill guide.
37. The instrument of example 28 wherein the first tunnel member comprises a bone punch.
38. The instrument of example 28 wherein the first tunnel member includes a relief opening through the side wall opposite the recess and communicating with the first longitudinal passage and recess.
39. The instrument of example 28 wherein the first tunnel member includes indicia on an outer surface and readable relative to a bone surface to indicate a depth of penetration of the first tunnel member into a bone corresponding to a predetermined tunnel depth.
40. The instrument of example 28 wherein the second tunnel member is separate from the guide body.
41. The instrument of example 40 wherein the second tunnel member engages the guide body in axial sliding relationship along the second guide axis.
42. The instrument of example 28 wherein the second tunnel member comprises a drill guide.
43. The instrument of example 28 wherein the second tunnel member comprises a bone punch.
44. The instrument of example 28 further comprising an angled surface at the distal end of the second longitudinal passage, the angled surface facing the opening, the angled surface operable to deflect the passer through the opening.
45. The instrument of example 28 wherein the passer comprises a first end and a second end, the passer defining a loop at its second end.
46. The instrument of example 45 wherein the passer is formed of a super elastic material.

47. The instrument of example 28 wherein the passer has a length greater than the combined length of the first and second longitudinal passages.

48. The instrument of example 45 wherein the loop is bent.

49. The instrument of example 28 wherein the passer comprises a relatively rigid shaft extending away from the first end, a relatively flexible wire attached to the shaft and extending away from the shaft to the second end.

50. An instrument for placing a member transosseously through first and second transverse, intersecting bone tunnels, the instrument comprising:
a guide body defining a first guide axis, a second guide axis, and a third guide axis, the second and third guide axes intersecting the first guide axis at a location spaced from the guide body, the second and third guide axes intersecting the first guide axis at the same location;
a first tunnel member engaged with the guide body coaxial with the first guide axis, the first tunnel member having a proximal end and a distal end, the first tunnel member having a first longitudinal passage at least partway through the first tunnel member, the first tunnel member including a first side wall and a first side opening in the first side wall nearer the distal end than the proximal end, the first longitudinal passage extending from the proximal end of the first tunnel member toward the distal end of the first tunnel member and communicating with the first side opening;
a second tunnel member engaged with the guide body coaxial with the second guide axis, the second tunnel member having a proximal end and a distal end, the second tunnel member having a second longitudinal passage at least partway through the second tunnel member, the second tunnel member including a second side wall and a second side opening in the second side wall nearer the distal end than the proximal end, the second longitudinal passage extending from the proximal end of the second tunnel member toward the distal end of the second tunnel member and communicating with the second side opening, the first tunnel member and second tunnel member being engageable at their distal ends so that the first side opening and second side opening are in communication with one another; and
a passer operable to extend from the proximal end of the second tunnel member, through the second side opening, through the first side opening, and to the proximal end of the first tunnel member in one continuous path.

51. The instrument of example 50 wherein the distal end of the second tunnel member is operable to insert into the first side opening with the second side opening in communication with the first side opening.

52. The instrument of example 50 further comprising an angled surface at the distal end of the second longitudinal passage, the angled surface facing the second side opening, the angled surface operable to deflect the passer through the second side opening.

What is claimed is:

1. An instrument for placing a member transosseously through first and second transverse, intersecting bone tunnels, the instrument comprising:
a guide body defining a first guide axis and a second guide axis, the first guide axis and the second guide axis intersecting at a location spaced from the guide body;
a first tunnel member engaged with the guide body coaxial with the first guide axis,
the first tunnel member having a proximal end a distal end, the first tunnel member being substantially linear such that the first guide axis extends through the proximal end and a distal most portion of the distal end of the first tunnel member, the first tunnel member having a first longitudinal passage at least partway through the first tunnel member;
a second tunnel member engaged with the guide body coaxial with the second guide axis, the second tunnel member having a proximal end and a distal end non-parallel to the distal end of the first tunnel member, the second tunnel member having a second longitudinal passage at least partway through the second tunnel member; and
a passer;
wherein the first tunnel member, the second tunnel member, and the passer, collectively, are configured such that the passer can be inserted, in one motion, from the proximal end of the second tunnel member, through the distal end of the second tunnel member, through the distal end of the first tunnel member, and to the proximal end of the first tunnel member.

2. The instrument of claim 1 wherein the first and second guide axes define a guide angle between them, the guide angle being adjustable.

3. The instrument of claim 1 further comprising third and fourth guide axes, the second, third, and fourth guide axes intersecting the first guide axis at the same location on the first guide axis.

4. The instrument of claim 1 wherein the first tunnel member is fixed to the guide body.

5. The instrument of claim 1 wherein the first tunnel member comprises a drill guide.

6. The instrument of claim 1 wherein the first tunnel member comprises a bone punch.

7. The instrument of claim 6 wherein the first tunnel member includes a first side wall and a first side opening in the first side wall nearer the distal end than the proximal end, the first longitudinal passage extending from the proximal end of the first tunnel member toward the distal end of the first tunnel member and communicating with the first side opening.

8. The instrument of claim 7 wherein the second guide axis passes through the first side opening.

9. The instrument of claim 7 wherein the first tunnel member includes a relief opening through the side wall opposite the first side opening and communicating with the first longitudinal passage and first side opening.

10. The instrument of claim 7 wherein the first tunnel member includes indicia on an outer surface and operable to align with a bone surface to indicate a depth of penetration of the first tunnel member into a bone corresponding to a predetermined tunnel depth.

11. The instrument of claim 1 wherein the second tunnel member is separate from the guide body and the second tunnel member engages the guide body in axial sliding relationship along the second guide axis.

12. The instrument of claim 1 wherein the second tunnel member comprises a drill guide.

13. The instrument of claim 1 wherein the second tunnel member comprises a bone punch.

14. The instrument of claim 13 wherein the second tunnel member includes a second side wall and a second side opening in the second side wall nearer the distal end than the proximal end, the second longitudinal passage extending from the proximal end of the second tunnel member toward the distal end of the second tunnel member and communicating with the second side opening.

15. The instrument of claim 14 wherein the first tunnel member includes a first side wall and a first side opening in the first side wall nearer the distal end than the proximal end, the first longitudinal passage extending from the proximal end of the first tunnel member toward the distal end of the first tunnel member and communicating with the first side opening, the first tunnel member and second tunnel member being engageable at their distal ends so that the first side opening and second side opening are in communication with one another.

16. The instrument of claim 15 wherein the distal end of the second tunnel member is operable to insert into the first side opening with the second side opening in communication with the first side opening.

17. The instrument of claim 16 further comprising an angled surface at the distal end of the second longitudinal passage, the angled surface facing the second side opening, the angled surface operable to deflect the passer through the second side opening.

18. The instrument of claim 1 wherein the passer comprises a first end and a second end, the passer defining a loop at its second end.

19. The instrument of claim 1 wherein the passer has a length greater than the combined length of the first and second longitudinal passages.

20. The instrument of claim 18 wherein the loop is bent.

21. The instrument of claim 18 wherein the passer comprises a shaft and a wire extending from the shaft, the shaft extending away from the first end, the shaft having a shaft length, the shaft being relatively rigid compared to the wire, the wire being attached to an end of the shaft and extending away from the shaft to the second end where the wire defines the loop, the wire having a wire length along which the wire extends from the rigid shaft, the wire being relatively flexible compared to the shaft.

22. The instrument of claim 21 wherein the passer further comprises an outer tube engaged with the shaft in axial sliding relationship and moveable relative to the shaft from a first position in which the outer tube encloses a portion of the wire length and a second position in which the outer tube encloses less of the wire length.

23. An instrument for placing a member transosseously through first and second transverse, intersecting bone tunnels in a bone, the instrument comprising:
 a guide body defining a first guide axis and a second guide axis, the first guide axis and the second guide axis intersecting at a location spaced from the guide body;
 a first tunnel member engageable with the guide body coaxial with the first guide axis, the first tunnel member having an outer surface, a proximal end, a distal end, and a first longitudinal passage at least partway through the first tunnel member, the first tunnel member being substantially linear such that the first guide axis extends through the proximal end and a distal most portion of the distal end of the first tunnel member, the first tunnel member outer surface having a recess formed therein and communicating with the first longitudinal passage;
 a second tunnel member engaged with the guide body coaxial with the second guide axis, the second tunnel member having an outer surface,
 a proximal end, a distal end nonparallel to the distal end of the tunnel member, and a second longitudinal passage at least partway through the second tunnel member, the second tunnel member outer surface having an opening formed therein and communicating with the second longitudinal passage, the recess of the first tunnel member being operable to receive the distal end of the second tunnel member with the opening communicating with the recess, wherein the first longitudinal passage, recess, opening, and second longitudinal passage form a continuous passage from the proximal end of the first tunnel member to the proximal end of the second tunnel member; and
 a passer operable to extend from the proximal end of the second tunnel member, through the second side opening, through the first side opening, and to the proximal end of the first tunnel member in one continuous path.

24. The instrument of claim 23 wherein the recess is transverse to the first guide axis and the opening is transverse to the second guide axis.

25. The instrument of claim 23 further comprising a passer having an elongate flexible portion operable to simultaneously extend through both the first and second longitudinal passages while the second tunnel member is received in the recess of the first tunnel.

26. An instrument for placing a member transosseously through first and second transverse, intersecting bone tunnels, the instrument comprising:
 a guide body defining a first guide axis, a second guide axis, and a third guide axis, the second and third guide axes intersecting the first guide axis at a location spaced from the guide body, the second and third guide axes intersecting the first guide axis at the same location;
 a first tunnel member engaged with the guide body coaxial with the first guide axis, the first tunnel member having a proximal end a distal end, the first tunnel member being substantially linear such that the first guide axis extends through the proximal end and a distal most portion of the distal end of the first tunnel member, the first tunnel member having a first longitudinal passage at least partway through the first tunnel member, the first tunnel member including a first side wall and a first side opening in the first side wall nearer the distal end than the proximal end, the first longitudinal passage extending from the proximal end of the first tunnel member toward the distal end of the first tunnel member and communicating with the first side opening;
 a second tunnel member selectively engageable with the guide body coaxial with one of the second and third guide axes, the second tunnel member having a proximal end and a distal end nonparallel to the distal end of the first tunnel member, the second tunnel member having a second longitudinal passage at least partway through the second tunnel member, the second tunnel member including a second side wall and a second side opening in the second side wall nearer the distal end than the proximal end, the second longitudinal passage extending from the proximal end of the second tunnel member toward the distal end of the second tunnel member and communicating with the second side opening, the first tunnel member and second tunnel member being engageable at their distal ends so that the first side opening and second side opening are in communication with one another; and
 a passer operable to extend from the proximal end of the second tunnel member, through the second side opening, through the first side opening, and to the proximal end of the first tunnel member in one continuous path.

27. The instrument of claim 26 wherein the distal end of the second tunnel member is operable to insert into the first side opening with the second side opening in communication with the first side opening.

28. The instrument of claim 27 further comprising an angled surface at the distal end of the second longitudinal passage, the angled surface facing the second side opening, the angled surface operable to deflect the passer through the second side opening.

29. An instrument for placing a member transosseously through first and second transverse, intersecting bone tunnels, the instrument comprising:

a guide body defining a first guide axis and a second guide axis, the first guide axis and the second guide axis intersecting at a location spaced from the guide body;

a first tunnel member engaged with the guide body coaxial with the first guide axis, the first tunnel member having a proximal end a distal end, the first tunnel member being substantially linear such that the first guide axis extends through the proximal end and a distal most portion of the distal end of the first tunnel member, the first tunnel member having a first longitudinal passage at least partway through the first tunnel member;

a second tunnel member engaged with the guide body coaxial with the second guide axis, the second tunnel member having a proximal end and a distal end non-parallel to the distal end of the first tunnel member, the second tunnel member having a second longitudinal passage at least partway through the second tunnel member; and a passer operable to extend from the proximal end of the second tunnel member, through the distal end of the second tunnel member, through the distal end of the first tunnel member, and to the proximal end of the first tunnel member;

wherein one of the first tunnel member and the second tunnel member comprises a feature that contacts the passer during motion of the passer through the second tunnel member and/or the first tunnel member, to direct the passer away from the second guide axis.

30. The instrument of claim 29, wherein:

the second tunnel member further comprises a second side wall and a second side opening in the second side wall nearer the distal end than the proximal end, the second longitudinal passage extending from the proximal end of the second tunnel member toward the distal end of the second tunnel member and communicating with the second side opening; and the feature comprises an angled surface at the distal end of the second longitudinal passage, the angled surface facing the second side opening, the angled surface operable to deflect the passer through the second side opening.

* * * * *